US010544224B2

(12) United States Patent
Manekas et al.

(10) Patent No.: US 10,544,224 B2
(45) Date of Patent: Jan. 28, 2020

(54) METHOD OF TREATING CANCER USING IMMUNE CHECKPOINT INHIBITOR

(71) Applicant: BRISTOL-MYERS SQUIBB COMPANY, Princeton, NJ (US)

(72) Inventors: Demetrios Manekas, Princeton, NJ (US); Joseph Grosso, Princeton, NJ (US); Jeffrey Anderson, Princeton, NJ (US)

(73) Assignee: Bristol-Myers Squibb Company, Priceton, NJ (US)

(*) Notice: Subject to any disclaimer, the term of this patent is extended or adjusted under 35 U.S.C. 154(b) by 164 days.

(21) Appl. No.: 15/210,612

(22) Filed: Jul. 14, 2016

(65) Prior Publication Data
US 2017/0037132 A1 Feb. 9, 2017

Related U.S. Application Data

(60) Provisional application No. 62/192,396, filed on Jul. 14, 2015.

(51) Int. Cl.
C07K 16/28 (2006.01)
A61K 39/395 (2006.01)
C07K 16/30 (2006.01)
A61K 39/00 (2006.01)
C12Q 1/70 (2006.01)
G01N 33/574 (2006.01)

(52) U.S. Cl.
CPC ...... C07K 16/2827 (2013.01); C07K 16/2818 (2013.01); C12Q 1/708 (2013.01); G01N 33/5743 (2013.01); A61K 2039/507 (2013.01); C07K 2317/21 (2013.01); C07K 2317/24 (2013.01); C07K 2317/51 (2013.01); C07K 2317/76 (2013.01); C07K 2317/92 (2013.01); C12Q 2600/158 (2013.01); G01N 2333/025 (2013.01)

(58) Field of Classification Search
None
See application file for complete search history.

(56) References Cited

U.S. PATENT DOCUMENTS

| 5,952,199 | A | 9/1999 | Davis-Smyth et al. |
| 5,977,318 | A | 11/1999 | Linsley et al. |
| 6,051,227 | A | 4/2000 | Allison et al. |
| 6,682,736 | B1 | 1/2004 | Hanson et al. |
| 6,808,710 | B1 | 10/2004 | Wood et al. |
| 6,984,720 | B1 | 1/2006 | Korman et al. |
| 7,034,121 | B2 | 4/2006 | Carreno et al. |
| 7,169,901 | B2 | 1/2007 | Baca et al. |
| 7,297,334 | B2 | 11/2007 | Baca et al. |
| 7,423,125 | B2 | 9/2008 | Alitalo et al. |
| 7,488,802 | B2 | 2/2009 | Collins et al. |
| 7,498,414 | B2 | 3/2009 | Zhu | |
| 7,595,048 | B2 | 9/2009 | Honjo et al. |
| 7,605,238 | B2 | 10/2009 | Korman et al. |
| 7,943,743 | B2 | 5/2011 | Korman et al. |
| 7,972,596 | B2 | 7/2011 | Wu et al. |
| 8,008,449 | B2 * | 8/2011 | Korman ............... C07K 16/18 530/388.15 |
| 8,034,905 | B2 | 10/2011 | Kavlie et al. |
| 8,168,179 | B2 | 5/2012 | Honjo et al. |
| 8,168,757 | B2 | 5/2012 | Finnefrock et al. |
| 8,217,149 | B2 | 7/2012 | Irving et al. |
| 8,354,509 | B2 | 1/2013 | Carven et al. |
| 8,383,796 | B2 | 2/2013 | Korman et al. |
| 8,609,089 | B2 | 12/2013 | Langermann et al. |
| 8,728,474 | B2 | 5/2014 | Honjo et al. |
| 8,779,105 | B2 | 7/2014 | Korman et al. |
| 8,779,108 | B2 | 7/2014 | Queva et al. |
| 8,900,587 | B2 | 12/2014 | Carven et al. |
| 9,067,999 | B1 | 6/2015 | Honjo et al. |
| 9,073,994 | B2 | 7/2015 | Honjo et al. |
| 9,084,776 | B2 | 7/2015 | Korman et al. |
| 9,102,725 | B2 | 8/2015 | Korman et al. |
| 9,212,224 | B2 | 12/2015 | Cogswell et al. |
| 9,273,135 | B2 | 3/2016 | Korman et al. |
| 9,358,289 | B2 | 6/2016 | Korman et al. |
| 9,387,247 | B2 | 7/2016 | Korman et al. |
| 9,393,301 | B2 | 7/2016 | Honjo et al. |
| 9,402,899 | B2 | 8/2016 | Honjo et al. |

(Continued)

FOREIGN PATENT DOCUMENTS

WO    WO-0044777 A1    8/2000
WO    WO-2006121168 A1    11/2006
(Continued)

OTHER PUBLICATIONS

Padlan (Advances in Protein Chemistry, 1996, 49:57-133).*
Corada (Blood, 2001; 97:1679-84).*
Tzartos et al. (Methods in Molecular Biology, 1996, 66:55-66).*
Kulkarni-Kale et al., Nucleic Acid Research, 2005, 33:W168-W171.*
Berglund et al., Protein Science, 2008, 17:606-613.*
Gildener-Leapman (Oral Oncology, 2013, 50:780-784).*
Green (Cancer Updates, 2015, pp. 1-6).*
Merck et al, (ClinicalTrials.gov, NCT01848834, 2017).*
Farashi-Bonab (MOJ Immunology, 2015, 2:00062(pp. 1-9)).*
Geibler et al. (Anticancer Research, 2013, 33:913-916).*
Kuenen et al. (Clinical Cancer Research, 2010, 16:1915-1923).*
Bristol-Myers Squibb (Clinical trial, NCT02105636, 2014).*
Bristol-Myers Squibb (Clinical trial, NCT01721772, 2012).*
Bristol-Myers Squibb (Clinical trial, NCT01673867, 2012).*

(Continued)

Primary Examiner — Julie Wu
(74) Attorney, Agent, or Firm — Sterne, Kessler, Goldstein & Fox P.L.L.C.

(57) ABSTRACT

This disclosure provides a method for treating HPV-positive squamous cell carcinoma of the head and neck comprising administering to the subject an immune checkpoint inhibitor, e.g., an anti-PD-1 antibody or an anti-PD-L1 antibody. The disclosure also provides a method for treating HPV-negative squamous cell carcinoma of the head and neck administering to the subject an immune checkpoint inhibitor, e.g., an anti-PD-1 antibody or an anti-PD-L1 antibody. The subject can be additionally administered another anti-cancer agent.

19 Claims, 1 Drawing Sheet

(56) References Cited

U.S. PATENT DOCUMENTS

| | | | |
|---|---|---|---|
| 9,492,539 | B2 | 11/2016 | Korman et al. |
| 9,492,540 | B2 | 11/2016 | Korman et al. |
| 9,856,320 | B2 | 1/2018 | Cogswell et al. |
| 10,138,299 | B2 | 11/2018 | Cogswell et al. |
| 10,266,594 | B1 | 4/2019 | Cogswell et al. |
| 10,266,595 | B2 | 4/2019 | Cogswell et al. |
| 10,266,596 | B1 | 4/2019 | Cogswell et al. |
| 10,308,714 | B2 | 6/2019 | Cogswell et al. |
| 10,316,091 | B2 | 6/2019 | Cogswell et al. |
| 2006/0110383 | A1 | 5/2006 | Honjo et al. |
| 2012/0263677 | A1 | 10/2012 | Eagle et al. |
| 2013/0017199 | A1 | 1/2013 | Langermann |
| 2014/0341917 | A1 | 11/2014 | Nastri et al. |
| 2014/0356353 | A1 | 12/2014 | Queva et al. |
| 2015/0079109 | A1 | 3/2015 | Li et al. |
| 2015/0210769 | A1* | 7/2015 | Freeman ............ C07K 16/2896 424/136.1 |
| 2015/0290316 | A1 | 10/2015 | Graziano et al. |
| 2016/0022814 | A1* | 1/2016 | Petit ................. A61K 39/39558 424/450 |
| 2016/0031990 | A1* | 2/2016 | Steele ................ C07K 16/2818 424/172.1 |
| 2016/0075782 | A1 | 3/2016 | Korman et al. |
| 2016/0090417 | A1 | 3/2016 | Cogswell et al. |
| 2016/0362495 | A1 | 12/2016 | Korman et al. |
| 2017/0051060 | A1 | 2/2017 | Honjo et al. |
| 2017/0088615 | A1 | 3/2017 | Korman et al. |
| 2018/0273624 | A1 | 9/2018 | Cogswell et al. |
| 2018/0282413 | A1 | 10/2018 | Cogswell et al. |
| 2018/0282414 | A1 | 10/2018 | Cogswell et al. |
| 2018/0312590 | A1 | 11/2018 | Cogswell et al. |
| 2018/0319887 | A1 | 11/2018 | Cogswell et al. |
| 2019/0092863 | A1 | 3/2019 | Cogswell et al. |
| 2019/0100589 | A1 | 4/2019 | Cogswell et al. |
| 2019/0100590 | A1 | 4/2019 | Cogswell et al. |
| 2019/0112376 | A1 | 4/2019 | Cogswell et al. |
| 2019/0112377 | A1 | 4/2019 | Cogswell et al. |
| 2019/0135920 | A1 | 5/2019 | Cogswell et al. |
| 2019/0153099 | A1 | 5/2019 | Cogswell et al. |

FOREIGN PATENT DOCUMENTS

| | | | |
|---|---|---|---|
| WO | WO-2007005874 | A2 | 1/2007 |
| WO | WO-2007113648 | A2 | 10/2007 |
| WO | WO-2010019570 | A2 | 2/2010 |
| WO | WO-2012122444 | A1 | 9/2012 |
| WO | WO-2012145493 | A1 | 10/2012 |
| WO | WO-2013173223 | A1 | 11/2013 |
| WO | WO-2016029073 | A2 | 2/2016 |

OTHER PUBLICATIONS

Ferris et al. (Radiation Oncology, 2018, 100:p. 1317; abstract LBA10).*

Brahmer, J.R., et al., "Safety and Activity of Anti-PD-L1 Antibody in Patients with Advanced Cancer," *The New England Journal of Medicine* 366(26):2455-2465, Massachusetts Medical Society, United States (2012).

Brahmer, J.R., et al., "Phase I Study of Single-agent Anti-programmed Death-1 (MDX-1106) in Refractory Solid Tumors: Safety, Clinical Activity, Pharmacodynamics, and Immunologic Correlates," *Journal of Clinical Oncology* 28(19):3167-3175, American Society of Clinical Oncology, United States (2010).

Burd, E.M., "Human Papillomavirus and Cervical Cancer," *Clinical Microbiology Reviews* 16(1):1-17, American Society for Microbiology, United States (2003).

Fury, M., et al., "Clinical Activity and Safety of MEDI4736, an Anti-PD-L1 Antibody, in Patients with Head and Neck Cancer," *Annals of Oncology* 25(4):iv341, Abstract 988PD, Oxford University Press, England, 2 pages. (Sep. 1, 2014).

GenBank, "cytotoxic T-lymphocyte-associated protein 4 [Homo sapiens]," Accession No. AAB59385.1, accessed at https://www.ncbi.nlm.nih.gov/protein/AAB59385, accessed on Dec. 1, 2016, 3 pages.

GenBank, "Human hPD-1 (hPD-1) mRNA, complete cds," Accession No. U64863.1, accessed at https://www.ncbi.nlm.nih.gov/nuccore/U64863, accessed on Dec. 1, 2016, 3 pages.

GenBank, "RecName: Full=Programmed cell death 1 ligand 1; Short=PD-L1; Short=PDCD1 ligand 1; Short=Programmed death ligand 1; AltName: Full=B7 homolog 1; Short=B7-H1; AltName: CD_antigen=CD274; Flags: Precursor," Accession No. Q9NZQ7.1, accessed at https://www.ncbi.nlm.nih.gov/protein/Q9NZQ7, accessed on Dec. 1, 2016, 11 pages.

Hamid, O. and Carvajal, R.D., "Anti-programmed Death-1 and Anti-programmed Death-ligand 1 Antibodies in Cancer Therapy," *Expert Opinion on Biological Therapy* 13(6):847-861, Informa UK, Ltd., England (2013).

Hamid, O., et al., "Safety and Tumor Responses with Lambrolizumab (Anti-PD-1) in Melanoma," *The New England Journal of Medicine* 369(2):134-144, Massachusetts Medical Society, United States of America (2013).

Hayes, D.N., et al., "Genetic Landscape of Human Papillomavirus-Associated Head and Neck Cancer and Comparison to Tobacco-Related Tumors," *Journal of Clinical Oncology* 33(29):3227-3234, American Society of Clinical Oncology, United States (Oct. 10, 2015).

Herbst, R.S., et al., "A Study of MPDL3280A, an Engineered PD-L1 Antibody in Patients with Locally Advanced or Metastatic Tumors," *Journal of Clinical Oncology* 31(*Suppl*):Abstract 3000, American Society of Clinical Oncology, United States, 2 pages (2013).

Herbst, R.S., et al., "Predictive Correlates of Response to the Anti-PD-L1 Antibody MPDL3280A in Cancer Patients," *Nature* 515(7528):563-567, Macmillan Publisher Limited, England (Nov. 27, 2014).

Hodi, F.S., et al., "Improved Survival with Ipilimumab in Patients with Metastatic Melanoma," *The New England Journal of Medicine* 363(8):711-723, Massachusetts Medical Society, United States (2010).

Ibrahim, R., et al., "PD-L1 Blockade for Cancer Treatment: MEDI4736," *Seminars in Oncology* 42(3):474-483, Elsevier Inc., United States (Feb. 25, 2015).

International Search Report and Written Opinion for International Application No. PCT/US2016/042297, European Patent Office, Netherlands, dated Dec. 23, 2016, 18 pages.

Johnson, D.B., et al., "Severe Cutaneous and Neurologic Toxicity in Melanoma Patients During Vemurafenib Administration Following Anti-PD-1 Therapy," *Cancer Immunology Research* 1(6):373-377, American Association for Cancer Research, United States (2013).

Keck, M.K., et al., "Integrative Analysis of Head and Neck Cancer Identifies Two Biologically Distinct HPV and Three Non-HPV Subtypes," *Clinical Cancer Research* 21(4):870-881, American Association for Cancer Research, United States (Feb. 15, 2015).

Khleif, S., et al., "MEDI4736, An Anti-PD-L1 Antibody with Modified Fc Domain: Preclinical Evaluation and Early Clinical Results from a Phase 1 Study in Patients with Advanced Solid Tumors," Abstract 802, in *Proceedings from the European Cancer Congress* 2013, Amsterdam, The Netherlands (Sep. 27-Oct. 1, 2013).

Lee, S.M. and Chow, L.Q., "A New Addition to the PD-1 Checkpoint Inhibitors for Non-small Cell Lung Cancer—the Anti-PDL1 Antibody-MEDI4736," *Translational Lung Cancer Research* 3(6):408-410, Translational Lung Cancer Research, China (Nov. 27, 2014).

McDermott, D.F. and Atkins, M.B., "PD-1 as a Potential Target in Cancer Therapy," *Cancer Medicine* 2(5):662-673, John Wiley & Sons Ltd., United States (2013).

NCI Drug Dictionary, "anti-PD-1 Fusion Protein AMP-224," accessed at https://www.cancer.gov/publications/dictionaries/cancer-drug?cdrid=700595, accessed on Dec. 1, 2016, 3 pages.

NCI Drug Dictionary, "anti-PD-1 monoclonal antibody MEDI0680," accessed at https://www.cancer.gov/publications/dictionaries/cancer-drug?cdrid=756047, accessed on Dec. 1, 2016, 3 pages.

NCI Drug Dictionary, "pembrolizumab," accessed at https://www.cancer.gov/drugdictionary?cancer-drug?cdrid=695789, accessed on Dec. 1, 2016, 3 pages.

(56) References Cited

OTHER PUBLICATIONS

Rini, B.I., et al., "Phase 1 Dose-escalation Trial of Tremelimumab Plus Sunitinib in Patients with Metastatic Renal Cell Carcinoma," *Cancer* 117(14):758-767, American Cancer Society, United States (2011).

Seiwert, T.Y., et al., "Safety and Clinical Activity of Pembrolizumab for Treatment of Recurrent or Metastatic Squamous Cell Carcinoma of the Head and Neck (KEYNOTE-012): An Open-label, Multicentre, Phase 1b Trial," *The Lancet Oncology* 17(7):956-965, Lancet Pub, England (May 27, 2016).

Seiwert, T.Y., et al., "Antitumor Activity and Safety of Pembrolizumab in Patients (Pts) with Advanced Squamous Cell Carcinoma of the Head and Neck (SCCHN): Preliminary Results from KEYNOTE-012 Expansion Cohort," *Journal of Clinical Oncology* 33(18):Abstract LBA6008, ASCO Meeting Abstracts, American Society of Clinical Oncology, United States (May 29-Jun. 2, 2015).

Sjoblom, T., et al., "The Consensus Coding Sequences of Human Breast and Colorectal Cancers," *Science* 314(5797):268-274, American Association for the Advancement of Science, United States (2006).

Stewart, R., et al., "Identification and Characterization of MEDI4736, an Antagonistic Anti-PD-L1 Monoclonal Antibody," *Cancer Immunology Research* 3(9):1052-1062, American Association for Cancer Research, United States (May 5, 2015).

Sunshine, J. and Taube, J.M., "PD-1/PD-L1 Inhibitors," *Current Opinion in Pharmacology* 23:32-38, Elsevier Ltd., England (Jun. 2, 2015).

Tabernero, J., et al., "Clinical Activity, Safety and Biomarkers of MPDL3280A, an Engineered PD-L1 Antibody in Patients with Locally Advanced or Metastatic Colorectal Cancer (CRC), Gastric Cancer (GC), Squamous cell Carcinoma of the Head and Neck (SCCHN) or Other Tumors," *Journal of Clinical Oncology* 31:Abstract 3622, Presented at the American Society of Clinical Oncology Meeting, Chicago, IL, 1 page (May 31-Jun. 4, 2013).

Taube, J.M., et al., "Colocalization of Inflammatory Response With B7-H1 Expression in Human Melanocytic Lesions Supports an Adaptive Resistance Mechanism of Immune Escape," *Science Translational Medicine* 4(127):127ra37, American Association for the Advancement of Science, United States, 22 pages (2012).

Topalian, S.L., et al., "Safety, Activity, and Immune Correlates of Anti-PD-1 Antibody in Cancer," *The New England Journal of Medicine* 366(26):2443-2454, Massachusetts Medical Society, United States (2012).

Topalian, S.L., et al., "Targeting the PD-1/B7-H1(PD-L1) Pathway to Activate Anti-tumor Immunity," *Current Opinion in Immunology* 24(2):207-212, Elsevier Ltd., England (2012).

Topalian, S.L., et al., "Survival, Durable Tumor Remission, and Long-term Safety in Patients with Advanced Melanoma Receiving Nivolumab," *Journal of Clinical Oncology* 32(10):1020-1030, American Society of Clinical Oncology, United States (Mar. 3, 2014).

United States Adopted Name (USAN) Drug Finder, "Pembrolizumab: Statement on a nonproprietary name adopted by the USAN Council (ZZ-165)," published Nov. 27, 2013, accessed at https://searchusan.ama-assn.org/usan/documentDownload?uri=%2Funstructured%2Fbinary%2Fusan%2Fpembrolizumab.pdf, accessed on Dec. 8, 2016, 2 pages.

Wang, C., et al., "In Vitro Characterization of the Anti-PD-1 Antibody Nivolumab, BMS-936558, and In Vivo Toxicology in Non-Human Primates," *Cancer Immunology Research* 2(9):846-856, American Association for Cancer Research, United States (May 28, 2014).

Wolchok, J.D., et al., "Nivolumab plus Ipilimumab in Advanced Melanoma," *The New England Journal of Medicine* 369(2):122-133, Massachusetts Medical Society, United States (2013).

Zandberg, D.P. and Strome, S.E., "The Role of the PD-L1:PD-1 Pathway in Squamous Cell Carcinoma of the Head and Neck," *Oral Oncology* 50(7):627-632, Elsevier Ltd., England (May 10, 2014).

Bai, S., et al., "A Guide to Rational Dosing of Monoclonal Antibodies," *Clin Pharmacokinetics* 51(2):119-135, Springer-Business, United States (Feb. 2012).

Ferris, R.L., et al., "Safety evaluation of nivolumab (Nivo) concomitant with cetuximab-radiotherapy for intermediate (IR) and high-risk (HR) local-regionally advanced head and neck squamous cell carcinoma (HNSCC): RTOG 3504," Presented Friday, Jun. 1, 2018, retrieved from: meetinglibrary.asco.org/record/160234/abstract, Sep. 10, 2018, 2 pages.

Guler, E., et al., "A review of the fixed douse use of new oral anticoagulants in obese patients: Is it really enough?," Anatol J Cardiol 15:1020-1029, Turkish Society of Cardiology, Turkey (Dec. 2015).

Pan, S-D., et al., "Weight-based dosing in medication use: what should we know?," Patient Preference and Adherence 10:549-560, Dove Medical Press, United Kingdom (Apr. 12, 2016).

Wang, D.D., et al., "Fixed Dosing Versus Body Size-Based Dosing of Monoclonal Antibodies in Adult Clinical Trials," J. Clin Pharmacol 49:1012-1024, John Wiley & Sons, United States (2009).

OPDIVO (nivolumab) [package insert], 32 pages; Bristol-Myers Squibb: Approved by U.S. Food and Drug Administration, United States; (Aug. 2018).

Clinical Trials.gov, NCT02764593, "Safety Testing of Adding Nivolumab to chemotherapy in Patients with Intermediated and High-Risk Local-Regionally Advanced Head and Neck Cancer," accessed at https://clinicaltrials.gov/ct2/show/NCT02764593, last accessed Sep. 13, 2018, 9 pages.

Office Action dated Jun. 22, 2018, in U.S. Appl. No. 15/141,769, Yang, A. et al., filed Apr. 28, 2016, 7 pages.

Office Action dated May 2, 2018, in U.S. Appl. No. 15/311,409, Feltquate, D. et al., filed Nov. 15, 2016, 13 pages.

Office Action dated Apr. 12, 2018, in U.S. Appl. No. 15/141,772, Yang, A. et al., filed Apr. 28, 2016, 13 pages.

Advisory Action dated Aug. 3, 2018, in U.S. Appl. No. 15/141,772, Yang, A. et al., filed Apr. 28, 2016, 3 pages.

Clinical Trials.gov, NCT01721772, "History of Changes for Study:NCT01721772: Study of Nivolumab (BMS-936558) Compared with Dacarbazine in Untreated, Unrespectable, or Metastatic Melanoma," accessed at https://clinicatrials.gov/ct2/history/NCT01721772?V_42=View, last accessed Jun. 11, 2019, 41 pages.

Clinical Trials.gov, NCT01673867, "History of Changes for Study: NCT01673867: Study of BMS-936558 (Nivolumab) Compared to Docetaxel in Previously Treated Metastatic Non-Sequamous NSCLC," accessed at https://clinicaltrials.gov/ct2/history/NCT01673867?V_55=View, last accessed Jun. 11, 2019, 50 pages.

\* cited by examiner

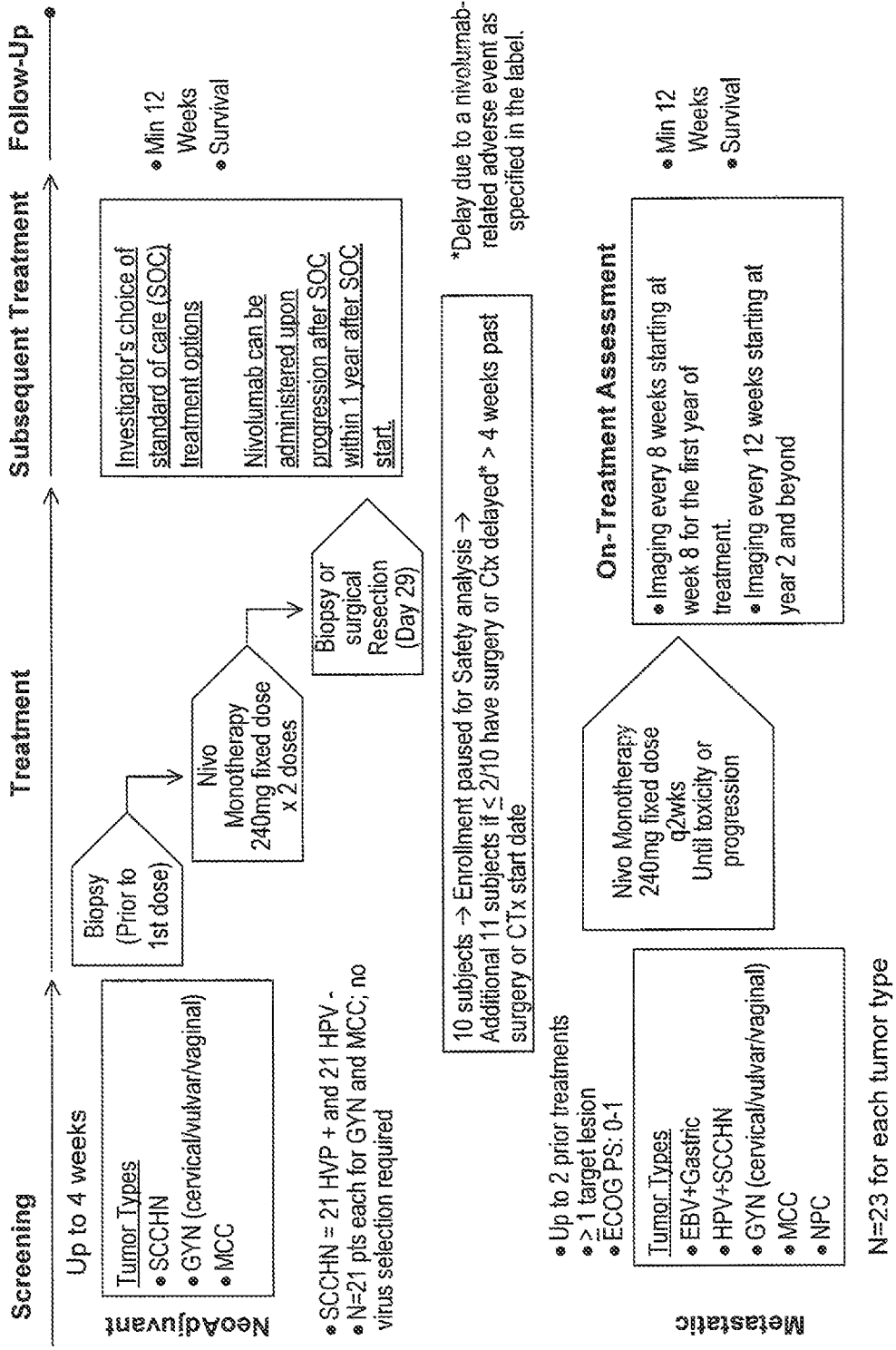

METHOD OF TREATING CANCER USING IMMUNE CHECKPOINT INHIBITOR

CROSS-REFERENCE TO RELATED APPLICATIONS

This application claims the benefit of U.S. Provisional Application Ser. No. 62/192,396 filed Jul. 14, 2015, which is incorporated herein by reference in its entirety.

Throughout this application, various publications are referenced in parentheses by author name and date, or by Patent No. or Patent Publication No. Full citations for these publications can be found at the end of the specification immediately preceding the claims. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

BACKGROUND OF THE INVENTION

Human cancers harbor numerous genetic and epigenetic alterations, generating neoantigens potentially recognizable by the immune system (Sjoblom et al. (2006) *Science* 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

Until recently, cancer immunotherapy had focused substantial effort on approaches that enhance anti-tumor immune responses by adoptive-transfer of activated effector cells, immunization against relevant antigens, or providing non-specific immune-stimulatory agents such as cytokines. In the past decade, however, intensive efforts to develop specific immune checkpoint pathway inhibitors have begun to provide new immunotherapeutic approaches for treating cancer, including the development of an antibody (Ab), ipilimumab (YERVOY®), that binds to and inhibits CTLA-4 for the treatment of patients with advanced melanoma (Hodi et al. (2010) *N Engl J Med* 363:711-23) and the development of antibodies such as nivolumab and pembrolizumab (formerly lambrolizumab; USAN Council Statement (2013) Pembrolizumab: Statement on a nonproprietary name adopted by the USAN Council (ZZ-165), Nov. 27, 2013) that bind specifically to the Programmed Death-1 (PD-1) receptor and block the inhibitory PD-1/PD-1 ligand pathway (Topalian et al. (2012a) *N Engl J Med* 366:2443-54; Topalian et al. (2012b) *Curr Opin Immunol* 24:207-12; Topalian et al. (2014) *J Clin Oncol* 32(10):1020-30; Hamid et al. (2013) *N Engl J Med* 369:134-144; Hamid and Carvajal (2013) *Expert Opin Biol Ther* 13(6):847-61; McDermott and Atkins (2013) *Cancer Med* 2(5):662-73).

PD-1 is a key immune checkpoint receptor expressed by activated T and B cells and mediates immunosuppression. Nivolumab (formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al. (2014) In vitro characterization of the anti-PD-1 antibody nivolumab, BMS-936558, and in vivo toxicology in non-human primates, *Cancer Imm Res*, in press). Nivolumab has been approved for the treatment of patients with unresectable or metastatic melanoma and disease progression following ipilimumab and, if BRAF V600 mutation positive, a BRAF inhibitor and for the treatment of squamous non-small cell lung cancer.

SUMMARY OF THE INVENTION

The present disclosure provides a method for treating a subject afflicted with a tumor derived from a human papilloma virus (HPV) positive squamous cell carcinoma head and neck cancer (SCCHN) comprising administering to the subject a therapeutically effective amount of: an antibody or an antigen-binding portion thereof that binds specifically to a Programmed Death-1 receptor (PD-1) or Programmed Death-Ligand 1 (PD-L1) and inhibits PD-1 activity ("anti-PD-1 antibody") or PD-L1 activity ("anti-PD-L1 antibody"), respectively.

The present disclosure also provides a method of treating a subject afflicted with a tumor derived from an HPV positive SCCHN comprising: (i) measuring a level of HPV in a sample of the subject, wherein the subject is positive for HPV and (ii) administering to the subject a therapeutically effective amount of an anti-PD-1 antibody or antigen-binding portion thereof or an anti-PD-L1 antibody or antigen-binding portion thereof.

The present disclosure also provides a method for identifying a subject afflicted with a tumor derived from an HPV positive SCCHN who is suitable for an anti-PD-1 antibody or anti-PD-L1 antibody therapy comprising measuring a level of HPV in a sample of the subject, wherein the subject is positive for HPV and wherein the subject is administered a therapeutically effective amount of an anti-PD-1 antibody or antigen-binding portion thereof or an anti-PD-L1 antibody or antigen-binding portion thereof.

The present disclosure also provides a method for identifying a subject afflicted with a tumor derived from an HPV positive SCCHN who is suitable for an anti-PD-1 antibody or anti-PD-L1 antibody therapy comprising: (i) measuring a level of HPV in a sample of the subject wherein the subject is positive for HPV and (ii) administering to the subject a therapeutically effective amount of an anti-PD-1 antibody or antigen-binding portion thereof or an anti-PD-L1 antibody or antigen-binding portion thereof.

In certain embodiments, the method further comprises administering one or more additional anti-cancer agents. In one particular embodiment, the anti-cancer agent is selected from the group consisting of an antibody or antigen-binding portion thereof that binds specifically to a CTLA-4 and inhibits CTLA-4 activity, a chemotherapy, a platinum-based doublet chemotherapy, a tyrosine kinase inhibitor, an anti-VEGF inhibitor, or any combination thereof.

The present disclosure also provides a method for treating a subject afflicted with a tumor derived from a human papilloma virus (HPV) negative squamous cell carcinoma head and neck cancer (SCCHN) comprising administering to the subject a therapeutically effective amount of: an antibody or an antigen-binding portion thereof that binds specifically to a Programmed Death-1 receptor (PD-1) or Programmed Death-Ligand 1 (PD-L1) and inhibits PD-1 activity ("anti-PD-1 antibody") or PD-L1 activity ("anti-PD-L1 antibody"), respectively.

The present disclosure also provides a method of treating a subject afflicted with a tumor derived from an HPV-negative SCCHN comprising: (i) measuring a level of HPV in a sample of the subject, wherein the subject is negative for HPV and (ii) administering to the subject a therapeutically effective amount of an anti-PD-1 antibody or antigen-binding portion thereof or an anti-PD-L1 antibody or antigen-binding portion thereof.

The present disclosure also provides a method for identifying a subject afflicted with a tumor derived from an HPV-negative SCCHN who is suitable for an anti-PD-1 antibody or an anti-PD-L1 antibody therapy comprising measuring a level of HPV in a sample of the subject, wherein the subject is negative for HPV and wherein the subject is administered a therapeutically effective amount of an anti-PD-1 antibody or antigen-binding portion thereof or an anti-PD-L1 antibody or antigen-binding portion thereof.

The present disclosure also provides method for identifying a subject afflicted with a tumor derived from an HPV negative SCCHN who is suitable for an anti-PD-1 antibody or anti-PD-L1 antibody therapy comprising: (i) measuring a level of HPV in a sample of the subject wherein the subject is negative for HPV and (ii) administering to the subject a therapeutically effective amount of an anti-PD-1 antibody or antigen-binding portion thereof or an anti-PD-L1 antibody or antigen-binding portion thereof.

The present disclosure also provides a kit for treating a subject afflicted with a tumor derived from an HPV positive SCCHN, the kit comprising: (a) an anti-PD-1 antibody or antigen-binding portion thereof or an anti-PD-L1 antibody or antigen-binding portion thereof; (b) instructions for determining the HPV positively of the tumor and, if the tumor is positive for HPV, administering the anti-PD-1 antibody or antigen-binding portion thereof or the anti-PD-L1 antibody or antigen-binding portion thereof to the subject in the methods described herein.

The present disclosure also provides a kit for treating a subject afflicted with a tumor derived from an HPV negative SCCHN, the kit comprising: (a) an anti-PD-1 antibody or antigen-binding portion thereof or an anti-PD-L1 antibody or antigen-binding portion thereof; (b) instructions for determining the HPV negativity of the tumor and, if the tumor is negative for HPV, administering the anti-PD-1 antibody or antigen-binding portion thereof or the anti-PD-L1 antibody or antigen-binding portion thereof to the subject in the methods described herein.

BRIEF DESCRIPTION OF THE DRAWINGS

FIG. 1 provides a schematic representation of a non-comparative, two-cohort, single-arm, open-label, phase 1/2 study of nivolumab in subjects with virus-positive and virus-negative solid tumors that will be performed to evaluate the safety, tolerability, and efficacy of nivolumab in subjects with select virus-positive and virus-negative tumors. The study is designed to have two cohorts: the neoadjuvant cohort ("neoadjuvant") and the metastatic/recurrent cohort ("metastatic").

DETAILED DESCRIPTION OF THE INVENTION

Terms

In order that the present disclosure can be more readily understood, certain terms are first defined. As used in this application, except as otherwise expressly provided herein, each of the following terms shall have the meaning set forth below. Additional definitions are set forth throughout the application.

"Administering" refers to the physical introduction of a composition comprising a therapeutic agent to a subject, using any of the various methods and delivery systems known to those skilled in the art. Routes of administration for the immune checkpoint inhibitors, e.g., the anti-PD-1 antibody or anti-PD-L1 antibody, include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the immune checkpoint inhibitors, e.g., the anti-PD-1 antibody or anti-PD-L1 antibody, is administered via a non-parenteral route, in some embodiments, orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. For example, an adverse event can be associated with activation of the immune system or expansion of immune system cells (e.g., T cells) in response to a treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

An immunoglobulin can derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. In certain embodiments, one or more amino acids of the isotype can be mutated to alter effector function. The term "antibody" includes, by way of example, both naturally occurring and non-naturally occurring Abs; monoclonal and polyclonal Abs; chimeric and humanized Abs; human or nonhuman Abs; wholly synthetic Abs; and single chain antibodies. A nonhuman antibody can be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

An "isolated antibody" refers to an antibody that is substantially free of other antibodies having different antigenic specificities (e.g., an isolated antibody that binds specifically to PD-1 is substantially free of antibodies that bind specifically to antigens other than PD-1). An isolated antibody that binds specifically to PD-1 can, however, have cross-reactivity to other antigens, such as PD-1 molecules from different species. Moreover, an isolated antibody can be substantially free of other cellular material and/or chemicals.

The term "monoclonal antibody" ("mAb") refers to a non-naturally occurring preparation of antibody molecules of single molecular composition, i.e., antibody molecules whose primary sequences are essentially identical, and which exhibits a single binding specificity and affinity for a particular epitope. A mAb is an example of an isolated antibody. MAbs can be produced by hybridoma, recombinant, transgenic or other techniques known to those skilled in the art.

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized antibody" refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen" antibody refers to an antibody that binds specifically to the antigen. For example, an anti-PD-1 antibody binds specifically to PD-1 and an anti-CTLA-4 antibody binds specifically to CTLA-4.

An "antigen-binding portion" of an antibody (also called an "antigen-binding fragment") refers to one or more fragments of an antibody that retain the ability to bind specifically to the antigen bound by the whole antibody.

A "cancer" refers a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. "Cancer" as used herein refers to primary, metastatic and recurrent cancers. In some embodiments, the cancer is a head and neck cancer. In further embodiments, the cancer is a squamous cell cancer of the head and neck. In some embodiments, the cancer is a human papillomavirus (HPV) positive cancer. In other embodiments, the cancer is an HPV negative cancer. In certain embodiments, the cancer is an HPV positive squamous cell cancer of the head and neck. In other embodiments, the cancer is an HPV negative squamous cell cancer of the head and neck. In yet other embodiments, the cancer is a nasopharyngeal carcinoma. In different embodiments, the cancer is Merkel cell carcinoma. In certain embodiments, the Merkel cell carcinoma is polyomavirus-associated. In other embodiments, the cancer is cervical, vaginal, or vulvar cancer. In certain embodiments, the cancer is an HPV positive cervical, vaginal, or vulvar cancer. In other embodiments, the cancer is an HPV negative cervical, vaginal, or vulvar cancer. In some embodiments, the cancer is a Epstein-Barr virus (EBV) positive cancer. In other embodiments, the cancer is an EBV negative cancer. In certain embodiments, the cancer is a gastric cancer, including gastroesophageal junction carcinoma (including adenocarcinoma from the lower esophagus). In further embodiments, the cancer is an EBV positive gastric cancer. In yet further embodiments, the cancer is an EBV negative gastric cancer. In other embodiments, the cancer is an EBV positive nasopharyngeal carcinoma. In further embodiments, the cancer is an EBV negative nasopharyngeal carcinoma.

"Cytotoxic T-Lymphocyte Antigen-4" (CTLA-4) refers to an immunoinhibitory receptor belonging to the CD28 family. CTLA-4 is expressed exclusively on T cells in vivo, and binds to two ligands, CD80 and CD86 (also called B7-1 and B7-2, respectively). The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. AAB59385.

"Dosing interval," as used herein, means the amount of time that elapses between multiple doses of a formulation disclosed herein being administered to a subject. Dosing interval can thus be indicated as ranges.

The term "dosing frequency" as used herein refers to the frequency of administering doses of a formulation disclosed herein in a given time. Dosing frequency can be indicated as the number of doses per a given time, e.g., once a week or once in two weeks.

"EBV positive" as used herein refers to a subject who has a cancer that is positive for Epstein-Barr virus (EBV; also known as human herpesvirus 4). "EBV negative" as used herein refers to a subject who has a cancer that is negative for EBV. In certain embodiments, the EBV status of the subject is determined using EBER (Epstein-Barr virus-encoded small RNAs) in situ hybridization to detect EBV-specific small RNAs, polymerase chain reaction (PCR) to amplify and detect EBV-specific DNA, or any other method known in the art. In certain embodiments, more than at least about 5%, at least about 10%, at least about 15%, at least about 20%, at least about 25%, at least about 30%, at least about 35%, at least about 40%, at least about 45% at least about 50%, at least about 55%, at least about 60%, at least about 65%, at least about 70%, at least about 75%, at least about 80%, at least about 85%, at least about 90%, at least about 95%, at least about 99%, or at least about 100% of the tumor cells show nuclear staining for EBER in an in situ hybridization, and the tumors are considered EBV-positive. In one embodiment, more than at least about 5% of the tumor cells show nuclear staining for EBER in an in situ hybridization, and the tumors are considered EBV-positive. In another embodiment, more than at least about 50% of the tumor cells show nuclear staining for EBER in an in situ hybridization, and the tumors are considered EBV-positive. In other embodiments, equal to or less than about 5%, about 4%, about 3%, about 2%, or about 1% of the tumor cells show nuclear staining for EBER in an in situ hybridization, and the tumors are considered EBV-negative. In further embodiments, equal to or less than 5% of the tumor cells show nuclear staining for EBER in an in situ hybridization, and the tumors are considered EBV-negative.

"Polyomavirus positive" or "polyomavirus associated" as used herein refers to a subject who has a cancer that is positive for a polyomavirus. Polyomaviruses are small, non-enveloped DNA viruses, some of which have been found to be associated with certain types of cancers. Merkel cell polyomavirus (MCPyV) has been found in tumor cells of squamous cell cancer of the skin, basal cell carcinoma, Bowen's disease, non-small cell lung carcinoma, and cervical cancer. In certain embodiments, the polyomavirus status of the subject is determined using PCR (including but not limited to real-time PCR and reverse transcription PCR) with primers directed to polyomavirus DNA, immunohistochemistry against polyomavirus-specific proteins, or any other method known in the art. In certain embodiments, more than at least about 5%, at least about 10%, at least about 15%, at least about 20%, at least about 25%, at least about 30%, at least about 35%, at least about 40%, at least about 45% at least about 50%, at least about 55%, at least about 60%, at least about 65%, at least about 70%, at least about 75%, at least about 80%, at least about 85%, at least about 90%, at least about 95%, at least about 99%, or at least about 100% of the tumor cells show strong and diffuse nuclear and/or cytoplasmic staining by an immunohistochemistry against one or more polyomavirus-specific antigens, and the tumors are considered polyomavirus-positive. In one embodiment, more than at least about 5% of the tumor cells show strong and diffuse nuclear and/or cytoplasmic staining by an immunohistochemistry against one or more polyomavirus-specific antigens, and the tumors are considered polyomavirus-positive. In another embodiment, more than at least about 50% of the tumor cells show strong and diffuse nuclear and/or cytoplasmic staining by an immu-nohistochemistry against one or more polyomavirus-specific antigens, and the tumors are considered polyomavirus-positive. In other embodiments, equal to or less than about 5%, about 4%, about 3%, about 2%, or about 1% of the tumor cells show strong and diffuse nuclear and/or cytoplasmic staining by an immunohistochemistry against one or more polyomavirus-specific antigens, and the tumors are considered polyomavirus-negative. In further embodiments, equal to or less than 5% of the tumor cells show strong and diffuse nuclear and/or cytoplasmic staining by an immunohistochemistry against one or more polyomavirus-specific antigens, and the tumors are considered polyomavirus-negative.

The use of the term "flat dose" means a dose that is administered to a patient without regard for the weight or body surface area (BSA) of the patient. The flat dose is therefore not provided as a mg/kg dose, but rather as an absolute amount of the agent (e.g., the anti-PD-1 antibody). For example, a 60 kg person and a 100 kg person would receive the same dose of the antibody (e.g., 240 mg of an anti-PD-1 antibody).

The use of the term "fixed dose" with regard to a composition of the invention means that two or more different antibodies in a single composition are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody to mg second antibody. For example, the 3:1 ratio of a first antibody and a second antibody can mean that a vial can contain about 240 mg of the first antibody and 80 mg of the second antibody or about 3 mg/ml of the first antibody and 1 mg/ml of the second antibody.

The term "weight based dose" as referred to herein means that a dose that is administered to a patient is calculated based on the weight of the patient. For example, when a patient with 60 kg body weight requires 3 mg/kg of an anti-PD-1 antibody in combination with 1 mg/kg of an anti-CTLA-4 antibody, one can draw the appropriate amounts of the anti-PD-1 antibody (i.e., 180 mg) and the anti-CTLA-4 antibody (i.e., 60 mg) at once from a 3:1 ratio fixed dosing formulation of an anti-PD-1 antibody and an anti-CTLA-4 antibody.

"HPV" as used herein refers to human papillomavirus. HPVs are a group of more than 200 viruses. Low-risk HPVs do not cause cancer. High-risk HPVs can cause cancer. In some embodiments, the HPV subtype can be any type of HPV. In certain embodiments, the HPV is HPV subtype 16, 18, 31, 33, 35, 39, 45, 51, 52, 56, 58, 59, 66, 68, or any combination thereof.

"HPV-positive" as used herein refers to a subject who has a cancer that is positive for HPV. "HPV-negative" as used herein refers to a subject who has a cancer that is negative for HPV. In certain embodiments, determining the HPV status of the subject comprises determining if a cancer tumor expresses one or more proteins derived from an HPV or a nucleotide sequence encoding the one or more proteins. In certain embodiments, more than at least about 50%, at least about 55%, at least about 60%, at least about 65%, at least about 70%, at least about 75%, at least about 80%, at least about 85%, at least about 90%, at least about 95%, at least about 99%, or at least about 100% of the tumor cells show strong and diffuse nuclear and cytoplasmic staining by an immunohistochemistry against p16 and the tumors are considered HPV-positive. In specific embodiments, more than at least about 70% of the tumor cells show strong and diffuse nuclear and cytoplasmic staining by an immunohistochemistry against p16 and the tumors are considered HPV-positive. In certain embodiments, equal to or less than about 30%, about 25%, about 20%, about 15%, about 10%, about 5% or about 1% of the tumor cells show strong and diffuse nuclear and cytoplasmic staining by an immunohistochemistry against p16 and the tumors are considered HPV-negative. In further embodiments, equal to or less than 30% of the tumor cells show strong and diffuse nuclear and cytoplasmic staining by an immunohistochemistry against p16 and the tumors are considered HPV-negative.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

"PD-L1 positive" as used herein can be interchangeably used with "PD-L1 expression of at least about 1%." In one embodiment, the PD-L1 expression can be used by any methods known in the art. In another embodiment, the PD-L1 expression is measured by an automated IHC. PD-L1 positive tumor can thus have at least about 1%, at least about 2%, at least about 5%, at least about 10%, or at least about 20% of tumor cells expressing PD-L1 as measured by an automated IHC. In certain embodiments, "PD-L1 positive" means that there are at least 100 cells that express PD-L1 on the surface of the cells.

"Programmed Death-1 (PD-1)" refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1 (PD-L1)" is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

A "subject" includes any human or nonhuman animal. The term "nonhuman animal" includes, but is not limited to, vertebrates such as nonhuman primates, sheep, dogs, and rodents such as mice, rats and guinea pigs. In some embodiments, the subject is a human. The terms, "subject" and "patient" are used interchangeably herein.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

As used herein, "subtherapeutic dose" means a dose of a therapeutic compound (e.g., an antibody) that is lower than the usual or typical dose of the therapeutic compound when administered alone for the treatment of a hyperproliferative disease (e.g., cancer).

By way of example, an "anti-cancer agent" promotes cancer regression in a subject or prevents further tumor growth. In certain embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of an anti-cancer agent can inhibit cell growth or tumor growth by at least about 10%, at least about 20%, by at least about 40%, by at least about 60%, or by at least about 80% relative to untreated subjects or, in certain embodiments, relative to patients treated with a standard-of-care therapy. In other embodiments of the invention, tumor regression can be observed and continue for a period of at least about 20 days, at least about 40 days, or at least about 60 days. Notwithstanding these ultimate measurements of therapeutic effectiveness, evaluation of immunotherapeutic drugs must also make allowance for "immune-related" response patterns.

An "immune-related" response pattern refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

A therapeutically effective amount of a drug includes a "prophylactically effective amount," which is any amount of the drug that, when administered alone or in combination with an anti-neoplastic agent to a subject at risk of developing a cancer (e.g., a subject having a pre-malignant condition) or of suffering a recurrence of cancer, inhibits the development or recurrence of the cancer. In certain embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The terms "once about every week," "once about every two weeks," or any other similar dosing interval terms as used herein mean approximate numbers. "Once about every week" can include every seven days±one day, i.e., every six days to every eight days. "Once about every two weeks" can include every fourteen days±three days, i.e., every eleven days to every seventeen days. Similar approximations apply, for example, to once about every three weeks, once about every four weeks, once about every five weeks, once about every six weeks and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively. A similar principle is applied to phrases including, but not limited to, "about once every two weeks", "about once every month", etc. . . .

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the invention are described in further detail in the following subsections.

Methods of the Invention

This disclosure provides methods of treating cancer associated with, derived from or caused by a virus using one or more immune checkpoint inhibitors (e.g., an anti PD-1 antibody or antigen-binding portion thereof or an anti-PD-L1 antibody or antigen binding portion thereof) as monotherapies or in combination with other anti-cancer agents. In one embodiment, the cancer is a solid tumor. In another embodiment, the cancer is a primary cancer. In other embodiments, the cancer is a metastatic or recurrent cancer. In some embodiments, the subject is a human patient. In certain embodiments, the subject is a chemotherapy-naïve patient (e.g., a patient who has not previously received any chemotherapy). In other embodiments, the subject has received another cancer therapy (e.g., a chemotherapy), but is resistant or refractory to such another cancer therapy.

In some embodiments, the invention is directed to a method of treating a subject afflicted with a tumor associated with, derived from or caused by an HPV, said method comprising administering a therapeutically effective amount of an immune checkpoint inhibitor (e.g., anti PD-1 antibody or antigen-binding portion thereof or anti-PD-L1 antibody or antigen binding portion thereof) as a monotherapy or in combination with one or more anti-cancer agents. In certain embodiments, the invention includes a method of treating an HPV positive tumor comprising administering an immune checkpoint inhibitor (e.g., anti PD-1 antibody or antigen-binding portion thereof or anti-PD-L1 antibody or antigen binding portion thereof). HPV contributes as a causal factor in several types of cancer, including cervical cancer, anal cancer, head and neck cancer (including oropharyngeal cancer), vaginal cancer, vulvar cancer, and penile cancer. Five percent of all cancers worldwide are caused by HPV. In some embodiments, the methods of the invention relate to a method of identifying a subject with an HPV-positive cancer. There are more than 200 related viruses in the HPV family, including subtypes 6, 11, 16, 18, 30, 31, 33, 34, 35, 39, 40, 42, 43, 44, 45, 51, 52, 53, 54, 55, 56, 57, 58, 59, 66, 68, and other unidentified subtypes. In some embodiments, the HPV subtype is HPV subtype 16, 18, 31, 33, 35, 39, 45, 51, 52, 56, 58, 59, 66, 68, or any combination thereof. In some embodiments, the HPV subtype is HPV subtype 16. In some embodiments, the HPV subtype is HPV subtype 18. In certain embodiments, more than at least about 50%, at least about 55%, at least about 60%, at least about 65%, at least about 70%, at least about 75%, at least about 80%, at least about 85%, at least about 90%, at least about 95%, at least about 99%, or at least about 100% of the tumor cells show strong and diffuse nuclear and cytoplasmic staining by an immunohistochemistry against p16 and the tumors are considered HPV-positive. In specific embodiments, more than at least about 70% of the tumor cells show strong and diffuse nuclear and cytoplasmic staining by an immunohistochemistry against p16 and the tumors are considered HPV-positive.

In certain embodiments, the invention provides a method for treating a subject afflicted with a tumor derived from an HPV positive squamous cell carcinoma head and neck cancer (SCCHN) comprising administering to the subject a therapeutically effective amount of an immune checkpoint inhibitor, e.g., an anti-PD-1 antibody or an anti-PD-L1 antibody. In some embodiments, the invention is directed to a method of treating a subject afflicted with a tumor derived from an HPV positive SCCHN comprising: (i) measuring a level of HPV in a sample of the subject, wherein the subject is positive for HPV and (ii) administering to the subject a therapeutically effective amount of an immune checkpoint inhibitor, e.g., an anti-PD-1 antibody or antigen-binding portion thereof or an anti-PD-L1 antibody or antigen-binding portion thereof. In certain embodiments, the anti-PD-1 antibody is nivolumab. In other embodiments, the anti-PD-1 antibody competes for binding with nivolumab. In further embodiments, the anti-PD-1 antibody is pembrolizumab. In still further embodiments, the anti-PD-1 antibody competes for binding with pembrolizumab. In other embodiments, the anti-PD-1 antibody is BGB-A317 or competes for binding with BGB-A317. In some embodiments, the PD-L1 antibody is BMS-936559, MPDL3280A, MEDI4736 or MSB0010718C or competes for binding with BMS-936559, MPDL3280A, MEDI4736 or MSB0010718C.

In certain embodiments, the invention is directed to a method for identifying a subject afflicted with a tumor derived from an HPV positive SCCHN who is suitable for an immune checkpoint inhibitor therapy, e.g., an anti-PD-1 antibody or anti-PD-L1 antibody therapy, comprising measuring a level of HPV in a sample of the subject, wherein the subject is positive for HPV and wherein the subject is administered a therapeutically effective amount of an immune checkpoint inhibitor, e.g., an anti-PD-1 antibody or antigen-binding portion thereof or an anti-PD-L1 antibody or antigen-binding portion thereof. In some embodiments, the invention is directed to a method for identifying a subject afflicted with a tumor derived from an HPV positive SCCHN who is suitable for an immune checkpoint inhibitor, e.g., an anti-PD-1 antibody or anti-PD-L1 antibody therapy comprising: (i) measuring a level of HPV in a sample of the subject wherein the subject is positive for HPV and (ii) administering to the subject a therapeutically effective amount of an immune checkpoint inhibitor, e.g., an anti-PD-1 antibody or antigen-binding portion thereof or an anti-PD-L1 antibody or antigen-binding portion thereof.

In some embodiments, the cancers treated by the methods disclosed herein are HPV-negative. In certain embodiments, the invention is directed to a method of treating a subject afflicted with an HPV negative tumor comprising administering a therapeutically effective amount of an immune checkpoint inhibitor (e.g., anti PD-1 antibody or antigen-binding portion thereof or anti-PD-L1 antibody or antigen binding portion thereof) as a monotherapy or in combination with one or more anti-cancer agents. In certain embodiments, the methods of the invention relate to a method of identifying a subject with an HPV-negative cancer. In certain embodiments, equal to or less than about 30%, about 25%, about 20%, about 15%, about 10%, about 5% or about 1% of the tumor cells show strong and diffuse nuclear and cytoplasmic staining by an immunohistochemistry against p16 and the tumors are considered HPV-negative. In further embodiments, equal to or less than 30% of the tumor cells show strong and diffuse nuclear and cytoplasmic staining by an immunohistochemistry against p16 and the tumors are considered HPV-negative.

In certain embodiments, the invention provides a method for treating a subject afflicted with a tumor derived from an HPV negative SCCHN comprising administering to the subject a therapeutically effective amount of: an immune checkpoint inhibitor, e.g., anti-PD-1 antibody or an anti-PD-L1 antibody. In some embodiments, the invention is directed to a method of treating a subject afflicted with a tumor derived from an HPV negative SCCHN comprising: (i) measuring a level of HPV in a sample of the subject, wherein the subject is negative for HPV and (ii) administering to the subject a therapeutically effective amount of an immune checkpoint inhibitor, e.g., anti-PD-1 antibody or antigen-binding portion thereof or an anti-PD-L1 antibody or antigen-binding portion thereof. In certain embodiments, the anti-PD-1 antibody is nivolumab. In other embodiments, the anti-PD-1 antibody competes for binding with nivolumab. In further embodiments, the anti-PD-1 antibody is pembrolizumab. In still further embodiments, the anti-PD-1 antibody competes for binding with pembrolizumab. In other embodiments, the anti-PD-1 antibody is BGB-A317 or competes for binding with BGB-A317. In other embodiments, the PD-L1 antibody is BMS-936559, MPDL3280A, MEDI4736 or MSB0010718C or competes for binding with BMS-936559, MPDL3280A, MEDI4736 or MSB0010718C.

In some embodiments, the invention is directed to a method for identifying a subject afflicted with a tumor derived from an HPV-negative SCCHN who is suitable for an immune checkpoint inhibitor therapy, e.g., an anti-PD-1 antibody or an anti-PD-L1 antibody comprising measuring a level of HPV in a sample of the subject, wherein the subject is negative for HPV and wherein the subject is administered a therapeutically effective amount of an immune checkpoint inhibitor therapy, e.g., an anti-PD-1 antibody or antigen-binding portion thereof or an anti-PD-L1 antibody or antigen-binding portion thereof. In some embodiments, the invention is directed to a method for identifying a subject afflicted with a tumor derived from an HPV negative SCCHN who is suitable for an immune checkpoint inhibitor therapy, e.g., an anti-PD-1 antibody or anti-PD-L1 antibody therapy comprising: (i) measuring a level of HPV in a sample of the subject wherein the subject is negative for HPV and (ii) administering to the subject a therapeutically effective amount of an immune checkpoint inhibitor therapy, e.g., an anti-PD-1 antibody or antigen-binding portion thereof or an anti-PD-L1 antibody or antigen-binding portion thereof.

In certain embodiments, the measuring of HPV disclosed herein comprises identifying the expression of one or more proteins derived from an HPV or a nucleotide sequence encoding the one or more proteins. In further embodiments, the one or more proteins derived from an HPV comprise p16, Ki-67, Cyclin D1, p53, ProEx C, E6, E7, or any combination thereof. In yet further embodiments, the nucleotide sequence encodes p16, Ki-67, Cyclin D1, p53, ProEx C, E6, E7, or any combination thereof.

In other embodiments, the one or more proteins derived from an HPV are identified by an immunohistochemistry method, an ELISA, a western blot or a protein array or any other assay known in the art. In other embodiments, the nucleotide sequence is identified by an in situ hybridization method, a DNA or RNA array or nucleotide hybridization technique, a tumor sequencing technique, or a quantitative polymerase chain reaction (PCR) or any other assay known in the art. See, e.g., Burd, E., Clin. Microbiol. Rev. 2003 January; 16(1): 1-17. In some embodiments, HPV DNA is detected with type-specific PCR, general primer PCR, or liquid hybridization. In certain embodiments, mRNA is tested using the In-Cell (Invirion, Frankfurt, Mich.) viral load test. In further embodiments, the measurement of HPV comprises monolayer cytology or histopathology. In still further embodiments, the measurement of HPV is performed using any assay known in the art. In certain embodiments, the sample comprises the primary tumor or a metastatic lymph node.

In certain embodiments, the cancer treated by the present invention is an EBV-positive cancer. In certain embodiments, the invention is directed to using immune checkpoint inhibitors (e.g., PD-1 antibodies or antigen-binding portions thereof or PD-L1 antibodies or antigen binding portions thereof) as monotherapies or in combination with other anti-cancer agents for the treatment of EBV-positive cancers. EBV is an enveloped virus and a member of the herpesvirus family. Cancers believed to be linked to EBV include, but are not limited to, nasopharyngeal carcinoma (NPC), gastric adenocarcinomas, high grade lymphomas (such as Burkitt lymphoma and some large B cell lymphomas), some Hodgkin lymphoma tumors, lymphomatoid granulomatosis, angioimmunoblastic T cell lymphoma, Peripheral T cell lymphoma, NK cell tumors and leukemias, and inflammatory pseudotumour-like follicular dendritic cell tumors. Treatment of EBV-associated tumors can include use of antivirals (including ganciclovir, famcyclovir, acyclovir, valaciclovir, foscarnet, and cidofovir) and immunotherapy (including the use of monoclonal antibodies, such as those directed to CD-20). In some embodiments, EBV-positive tumors that can be treated by the present invention include EBV-related gastric carcinoma and EBV-positive gastro-esophageal junction carcinoma, including adenocarcinoma arising from the lower esophagus. In certain embodiments of the invention, a subject with an EBV-related gastric carcinoma and EBV-positive gastro-esophageal junction carcinoma is administered an anti-PD-1 antibody or antigen-binding portion thereof or an anti-PD-L1 antibody or an antigen-binding portion thereof as a monotherapy or in any combination disclosed herein. Surgical resection of the cancerous tissue is the standard of care treatment for EBV-related gastric carcinoma. In one embodiment, a patient having EBV-related gastric carcinoma is administered nivolumab in addition to surgical resection. In another embodiment, a patient having an EBV-positive gastro-esophageal junction carcinoma is administered nivolumab in addition to surgical resection.

In certain embodiments, the cancers treated by the present invention are Polyomavirus-positive cancers. In certain embodiments, the invention is directed to using immune checkpoint inhibitors (e.g., PD-1 antibodies or antigen-binding portions thereof or PD-L1 antibodies or antigen binding portions thereof) as monotherapies or in combination with other anti-cancer agents for the treatment of polyomavirus-positive cancers. Polyomaviruses are DNA-based, non-enveloped viruses that have been linked to various tumors in humans. For example, Merkel cell polyomavirus (MCPyV) has been found in squamous cell cancer of the skin, basal cell carcinoma, Bowen's disease, non-small cell lung carcinoma, and cervical cancer. Merkel cell carcinoma (MCC), or neuroendocrine carcinoma of the skin, is a type of skin cancer that generally appears on a patient's face, head, or neck. The standard of care treatment for patients with MCC includes surgical resection for early disease followed by radiation therapy and chemotherapy for advanced disease. Chemotherapy drugs that can be used to treat MCC include, but are not limited to, etoposide and platinum-based drugs, including carboplatin. In one embodiment, a subject having a MCC tumor is administered an anti-PD-1 antibody or antigen-binding portion thereof or an anti-PD-L1 antibody or an antigen-binding portion thereof as a monotherapy or in any combination disclosed herein. In certain embodiments, a patient having an MCC tumor is administered nivolumab in addition to surgical resection, radiation therapy, chemotherapy, or a combination thereof.

Cervical, vaginal, and vulvar cancers can also be polyomavirus- and/or HPV-positive. In certain embodiments, the invention is directed to using immune checkpoint inhibitors (e.g., PD-1 antibodies or antigen-binding portions thereof or PD-L1 antibodies or antigen binding portions thereof) as monotherapies or in combination with other anti-cancer agents for the treatment of cervical, vaginal, and vulvar cancers. These tumors generally affect squamous cell populations of the respective tissues. Cervical cancers can include squamous cell carcinoma of the cervix as well as adenocarcinoma of the cervix, which affects the glandular and columnar cells lining the opening of the cervix and the endocervical canal. In certain embodiments, patients with cervical, vaginal or vulvar tumors are administered an anti-PD-1 antibody or antigen-binding portion thereof or an anti-PD-L1 antibody or an antigen-binding portion thereof as a monotherapy or in any combination disclosed herein. The standard of care treatment for patients with cervical cancer depends on the stage of the cancer, but often includes radical hysterectomy (surgical removal of the uterus, cervix, and some of the vagina). In some cases, patients can receive radiation therapy in combination with chemotherapy. The standard of care treatment for vaginal and vulvar cancers depend on the stage of treatment, but can include surgical resection for early disease and radiation in addition to chemotherapy for later stage tumors. Chemotherapy can include, but is not limited to, 5-FU or a platinum-based drug, such as cisplatin. In some embodiments, a patient having a polyomavirus- or HPV-positive cervical, vaginal, or vulvar tumor is administered nivolumab in addition to surgical resection and chemotherapy.

Nasopharyngeal carcinoma (NPC) is a cancer that develops in the nasopharynx. Previous exposure to Epstein-Barr virus (EBV) has been shown to increase a patient's chances of developing NPC. In certain embodiments, the invention is directed to using an immune checkpoint inhibitor (e.g., PD-1 antibody or antigen-binding portion thereof or PD-L1 antibody or antigen binding portion thereof) as a monotherapy or in combination with other anti-cancer agents for the treatment of NPC. In one embodiment, subjects with NPC are administered an anti-PD-1 antibody or antigen-binding portion thereof or an anti-PD-L1 antibody or an antigen-binding portion thereof as a monotherapy or in any combination disclosed herein. Early NPC is commonly treated with radiation therapy, which is supplemented in later stage tumors with chemotherapy, most often including 5-FU and a platinum-based drug, such as cisplatin. In certain embodiments, a patient having EPV-positive NPC is administered nivolumab in addition to radiation therapy and/or chemotherapy.

In other embodiments, the tumor further expresses PD-L1. The PD-L1 status of a tumor in a subject can be measured prior to administering any composition or utilizing any method disclosed herein. In one embodiment, the PD-L1 expression level of a tumor is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20% or greater than at least about 20%. In another embodiment, the PD-L1 status of a tumor is at least about 1%. In other embodiments, the PD-L1 status of the subject is at least about 5%. In a certain embodiment, the PD-L1 status of a tumor is at least about 10%. The measurement of PD-L1 status can be performed using an antibody, an in situ mRNA hybridization, an automated IHC method, or as described in Taube et al., "Colocalization of inflammatory response with B7-hl expression in human melanocytic lesions supports an adaptive resistance mechanism of immune escape," *Sci. Transl.*

Med. 4(127):127ra37 (2012) or U.S. Prov. Appl. Nos. 62/152,669, 62/153,954, and 62/167,674.

In certain embodiments, the therapy of the present invention (e.g., administration of an anti-PD-1 antibody or an anti-PD-L1 antibody and, optionally, another anti-cancer agent) effectively increases the duration of survival of the subject. In some embodiments, the anti-PD-1 antibody therapy or anti-PD-L1 antibody therapy of the present invention increases the duration of survival of the subject in comparison to standard-of-care therapies. In certain embodiments, the therapy of the invention increases the overall survival of the subject. In some embodiments, the subject exhibits an overall survival of at least about 10 months, at least about 11 months, at least about 12 months, at least about 13 months, at least about 14 months at least about 15 months, at least about 16 months, at least about 17 months, at least about 18 months, at least about 19 months, at least about 20 months, at least about 21 months, at least about 22 months, at least about 23 months, at least about 2 years, at least about 3 years, at least about 4 years, or at least about 5 years after the administration. In some embodiments, the duration of survival or the overall survival of the subject is increased by at least about 5%, at least about 10%, at least about 15%, at least about 20%, at least about 25%, at least about 30%, at least about 40%, at least about 50% or at least about 75% when compared to another subject treated with only a standard-of-care therapy. In other embodiments, the duration of survival or the overall survival of the subject is increased by at least about 1 month, at least about 2 months, at least about 3 months, at least about 4 months, at least about 6 months, at least about 1 year, at least about eighteen months, about least about 2 years, at least about 3 years, at least about 4 years or at least about 5 years when compared to another subject treated with only a standard-of-care therapy.

In certain embodiments, the therapy of the present invention effectively increases the duration of progression free survival of the subject. For example, the progression free survival of the subject is increased by at least about 2 weeks, at least about 1 month, at least about 2 months, at least about 3 months, at least about 4 months, at least about 6 months, or at least about 1 year when compared to another subject treated with only standard-of-care therapy. In certain embodiments, after the administration of an anti-PD-1 antibody or anti-PD-L1 antibody therapy, the subject exhibits an overall response rate of at least about 30%, 35%, 36%, 37%, 39%, 40%, 45%, or 50% compared to the response rate after administration of a standard-of-care therapy.

Immune Checkpoint Inhibitors (e.g., Anti-PD-1 Antibodies and Anti-PD-L1 Antibodies)

Immune checkpoint inhibitors suitable for use in the disclosed methods include anti-PD-1 antibodies that bind to PD-1 with high specificity and affinity, block the binding of PD-L1, and inhibit the immunosuppressive effect of the PD-1 signaling pathway. In any of the therapeutic methods disclosed herein, an anti-PD-1 or anti-PD-L1 "antibody" includes an antigen-binding portion that binds to the PD-1 or PD-L1 receptor, respectively, and exhibits the functional properties similar to those of whole antibodies in inhibiting ligand binding and upregulating the immune system. In certain embodiments, the anti-PD-1 antibody or antigen-binding portion thereof cross-competes with nivolumab for binding to human PD-1. In other embodiments, the anti-PD-L1 antibody or antigen-binding portion thereof competes for binding with BMS-936559, MPDL3280A, MEDI4736 or MSB0010718C for binding to human PD-L1.

In other embodiments, the anti-PD-1 antibody, anti-PD-L1 antibody, or antigen-binding portions thereof is a chimeric, humanized or human monoclonal antibody or a portion thereof. In certain embodiments for treating a human subject, the antibody is a humanized antibody. In other embodiments for treating a human subject, the antibody is a human antibody. Antibodies of an IgG1, IgG2, IgG3 or IgG4 isotype can be used.

In certain embodiments, the anti-PD-1 antibody, anti-PD-L1 antibody, or antigen-binding portions thereof comprises a heavy chain constant region which is of a human IgG1 or IgG4 isotype. In certain other embodiments, the sequence of the IgG4 heavy chain constant region of the anti-PD-1 antibody, anti-PD-L1 antibody, or antigen-binding portions thereof contain an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al., 2014 *Cancer Immunol Res.* 2(9):846-56). In yet other embodiments, the antibody comprises a light chain constant region which is a human kappa or lambda constant region. In other embodiments, the anti-PD-1 antibody, anti-PD-L1 antibody, or antigen-binding portions thereof is a mAb or an antigen-binding portion thereof.

HuMAbs that bind specifically to PD-1 with high affinity have been disclosed in U.S. Pat. No. 8,008,449. Other anti-PD-1 mAbs have been described in, for example, U.S. Pat. Nos. 6,808,710, 7,488,802, 8,168,757 and 8,354,509, and PCT Publication No. WO 2012/145493. Each of the anti-PD-1 HuMAbs disclosed in U.S. Pat. No. 8,008,449 has been demonstrated to exhibit one or more of the following characteristics: (a) binds to human PD-1 with a $K_D$ of $1 \times 10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and (j) inhibits tumor cell growth in vivo. Anti-PD-1 antibodies usable in the present invention include mAbs that bind specifically to human PD-1 and exhibit at least one, in some embodiments, at least five, of the preceding characteristics. In some embodiments, the anti-PD-1 antibody is nivolumab. In one embodiment, the anti-PD-1 antibody is pembrolizumab.

In one embodiment, the anti-PD-1 antibody is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al. In vitro characterization of the anti-PD-1 antibody nivolumab, BMS-936558, and in vivo toxicology in non-human primates, *Cancer Imm Res,* 2(9): 846-56 (2014)).

In another embodiment, the anti-PD-1 antibody or fragment thereof cross-competes with nivolumab. In other embodiments, the anti-PD-1 antibody or fragment thereof binds to the same epitope as nivolumab. In certain embodiments, the anti-PD-1 antibody has the same CDRs as nivolumab.

In another embodiment, the anti-PD-1 antibody or fragment thereof cross-competes with pembrolizumab. In some embodiments, the anti-PD-1 antibody or fragment thereof binds to the same epitope as pembrolizumab. In certain embodiments, the anti-PD-1 antibody has the same CDRs as pembrolizumab. In another embodiment, the anti-PD-1 antibody is pembrolizumab. Pembrolizumab (also known as "KEYTRUDA®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. Nos. 8,354,509 and 8,900,587; see also http://www.cancer.gov/drugdictionary?cdrid=695789 (last accessed: Dec. 14, 2014). Pembrolizumab has been approved by the FDA for the treatment of relapsed or refractory melanoma.

In other embodiments, the anti-PD-1 antibody or fragment thereof cross-competes with MEDI0608. In still other embodiments, the anti-PD-1 antibody or fragment thereof binds to the same epitope as MEDI0608. In certain embodiments, the anti-PD-1 antibody has the same CDRs as MEDI0608. In other embodiments, the anti-PD-1 antibody is MEDI0608 (formerly AMP-514), which is a monoclonal antibody. MEDI0608 is described, for example, in U.S. Pat. No. 8,609,089B2 or in http://www.cancer.gov/drugdictionary?cdrid=756047 (last accessed Dec. 14, 2014).

In certain embodiments, the first antibody is an anti-PD-1 antagonist. One example of the anti-PD-1 antagonist is AMP-224, which is a B7-DC Fc fusion protein. AMP-224 is discussed in U.S. Publ. No. 2013/0017199 or in http://www.cancer.gov/publications/dictionaries/cancer-drug?cdrid=700595 (last accessed Jul. 8, 2015).

In other embodiments, the anti-PD-1 antibody or fragment thereof cross-competes with BGB-A317. In some embodiments, the anti-PD-1 antibody or fragment thereof binds the same epitope as BGB-A317. In certain embodiments, the anti-PD-1 antibody has the same CDRs as BGB-A317. In certain embodiments, the anti-PD-1 antibody is BGB-A317, which is a humanized monoclonal antibody. BGB-A317 is described in U.S. Publ. No. 2015/0079109.

Anti-PD-1 antibodies usable in the disclosed methods also include isolated antibodies that bind specifically to human PD-1 and cross-compete for binding to human PD-1 with nivolumab (see, e.g., U.S. Pat. Nos. 8,008,449 and 8,779,105; WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of nivolumab by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 as, nivolumab are mAbs. For administration to human subjects, these cross-competing antibodies are chimeric antibodies, or humanized or human antibodies. Such chimeric, humanized or human mAbs can be prepared and isolated by methods well known in the art.

Anti-PD-1 antibodies usable in the methods of the disclosed invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab")$_2$ fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an antibody.

Anti-PD-1 antibodies suitable for use in the disclosed compositions are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and upregulating the immune system. In certain embodiments, the anti-PD-1 antibody or antigen-binding portion thereof cross-competes with nivolumab for binding to human PD-1. In other embodiments, the anti-PD-1 antibody or antigen-binding portion thereof is a chimeric, humanized or human monoclonal antibody or a portion thereof. In certain embodiments, the antibody is a humanized antibody. In other embodiments, the antibody is a human antibody. Antibodies of an IgG1, IgG2, IgG3 or IgG4 isotype can be used.

In certain embodiments, the anti-PD-1 antibody or antigen-binding portion thereof comprises a heavy chain constant region which is of a human IgG1 or IgG4 isotype. In certain other embodiments, the sequence of the IgG4 heavy chain constant region of the anti-PD-1 antibody or antigen-binding portion thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al. (2014)). In yet other embodiments, the antibody comprises a light chain constant region which is a human kappa or lambda constant region. In other embodiments, the anti-PD-1 antibody or antigen-binding portion thereof is a mAb or an antigen-binding portion thereof.

In certain embodiments of any of the therapeutic methods described herein comprising administration of an anti-PD-1 antibody, the anti-PD-1 antibody is nivolumab. In other embodiments, the anti-PD-1 antibody is pembrolizumab. In other embodiments, the anti-PD-1 antibody is chosen from the human antibodies 17D8, 2D3, 4H1, 4A11, 7D3 and 5F4 described in U.S. Pat. No. 8,008,449. In still other embodiments, the anti-PD-1 antibody is MEDI0608 (formerly AMP-514), AMP-224, or BGB-A317.

Anti-PD-1 antibodies usable in the methods of the disclosed invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an antibody.

In certain embodiments, an anti-PD-1 antibody used in the methods can be replaced with another PD-1 or anti-PD-L1 antagonist. For example, because an anti-PD-L1 antibody prevents interaction between PD-1 and PD-L1, thereby exerting similar effects to the signaling pathway of PD-1, an anti-PD-L1 antibody can replace the use of an anti-PD-1 antibody in the methods disclosed herein. Therefore, in one embodiment, the present invention is directed to a method for treating a subject afflicted with a tumor derived from an HPV positive SCCHN comprising administering to the subject a therapeutically effective amount an anti-PD-L1 antibody.

In certain embodiments, the anti-PD-L1 antibody is BMS-936559 (formerly 12A4 or MDX-1105) (see, e.g., U.S. Pat. No. 7,943,743; WO 2013/173223).

In other embodiments, the anti-PD-L1 antibody is MPDL3280A (also known as RG7446) (see, e.g., Herbst et al. (2013) J Clin Oncol 31(suppl):3000. Abstract.; U.S. Pat. No. 8,217,149).

In other embodiments, the anti-PD-L1 antibody is MEDI4736 (also called Durvalumab; Khleif (2013) In: Proceedings from the European Cancer Congress 2013; Sep. 27-Oct. 1, 2013; Amsterdam, The Netherlands. Abstract 802, See U.S. Pat. No. 8,779,108 or US 2014/0356353, filed May 6, 2014).

In further embodiments, the anti-PD-L1 antibody is MSB0010718C (also called Avelumab; See US 2014/0341917).

Because anti-PD-1 and anti-PD-L1 target the same signaling pathway and have been shown in clinical trials to exhibit similar levels of efficacy in a variety of cancers, including RCC (see Brahmer et al. (2012) N Engl J Med 366:2455-65; Topalian et al. (2012a) *N Engl J Med* 366: 2443-54; WO 2013/173223), an anti-PD-L1 antibody can be substituted for the anti-PD-1 antibody in any of the therapeutic methods disclosed herein. In certain embodiments, the anti-PD-L1 antibody is BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446) (see, e.g., Herbst et al. (2013) *J Clin Oncol* 31(suppl):3000. Abstract; U.S. Pat. No. 8,217,149) or MEDI4736 (Khleif (2013) In: Proceedings from the European Cancer Congress 2013; Sep. 27-Oct. 1, 2013; Amsterdam, The Netherlands. Abstract 802). In certain embodiments, the antibodies that cross-compete for binding to human PD-L1 with, or bind to the same epitope region of human PD-L1 as the above-references PD-L1 antibodies are mAbs. For administration to human subjects, these cross-competing antibodies can be chimeric antibodies, or can be humanized or human antibodies. Such chimeric, humanized or human mAbs can be prepared and isolated by methods well known in the art.

In some embodiments, an immune checkpoint inhibitor, e.g., an anti-PD-1 antagonist, used in the present invention is a PD-1 Fc fusion protein.

Combination Therapies with Anti-PD-1 or Anti-PD-L1 Antibodies

In certain embodiments, an immune checkpoint inhibitor (e.g., an anti-PD-1 antibody or anti-PD-L1 antibody) is administered in combination with one or more other anti-cancer agents. In certain embodiments, the one or more anti-cancer agents have been administered to the subject prior to the administration of the anti-PD-1 or anti-PD-L1 antibody or prior to the combination with the anti-PD-1 or anti-PD-L1 antibody. In certain embodiments, the one or more anti-cancer agents were not effective in treating the cancer. In some embodiments, the other anti-cancer agent is any anti-cancer agent described herein or known in the art. In certain embodiments, the other anti-cancer agent is an anti-CTLA-4 antibody. In one embodiment, the other anti-cancer agent is a chemotherapy or a platinum-based doublet chemotherapy (PT-DC). In certain embodiments, the other anti-cancer agent is an EGFR-targeted tyrosine kinase inhibitor (TKI). In one embodiment, the other anti-cancer agent is an anti-VEGF antibody. In other embodiments, the anti-cancer agent is a platinum agent (e.g., cisplatin, carboplatin), a mitotic inhibitor (e.g., paclitaxel, albumin-bound paclitaxel, docetaxel, taxotere, docecad), a fluorinated Vinca alkaloid (e.g., vinflunine, javlor), vinorelbine, vinblastine, etoposide, or pemetrexed gemcitabin. In one embodiment, the other anti-cancer agent is 5-flurouracil (5-FU). In certain embodiments, the other anti-cancer agent is any other anti-cancer agent known in the art. In some embodiments, two or more additional anti-cancer agents are administered in combination with the anti-PD-1 or anti-PD-L1 antibody. In some embodiments, the PD-1 or PD-L1 antibody is combined with surgical resection and/or radiation therapy.

In certain embodiments, the anti-PD-1 antibody or anti-PD-L1 antibody can be combined with another immunotherapy. In certain embodiments, immunotherapy involving blockade of immune checkpoints is administered as a monotherapy. In other embodiments, immunotherapy involving blockade of immune checkpoints is administered in combination with other therapies. In some embodiments, HPV positive SCCHN patients can benefit from the combination of different immunotherapeutic drugs.

Anti-CTLA-4 Antibodies

In certain embodiments, an anti-PD-1 antibody or anti-PD-L1 antibody is combined with an anti-CTLA-4 antibody. Anti-CTLA-4 antibodies useful for the combination can bind to human CTLA-4 so as to disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing or prolonging an immune response.

HuMAbs that bind specifically to CTLA-4 with high affinity have been disclosed in U.S. Pat. Nos. 6,984,720 and 7,605,238. Other CTLA-4 mAbs have been described in, for example, U.S. Pat. Nos. 5,977,318, 6,051,227, 6,682,736, and 7,034,121. The CTLA-4 HuMAbs disclosed in U.S. Pat. Nos. 6,984,720 and 7,605,238 have been demonstrated to exhibit one or more of the following characteristics: (a) binds specifically to human CTLA-4 with a binding affinity reflected by an equilibrium association constant ($K_a$) of at least about $10^7$ $M^{-1}$, or about $10^9$ $M^{-1}$, or about $10^{10}$ $M^{-1}$ to $10^{11}$ $M^{-1}$ or higher, as determined by Biacore analysis; (b) a kinetic association constant ($k_a$) of at least about $10^3$, about $10^4$, or about $10^5$ $m^{-1}$ $s^{-1}$; (c) a kinetic disassociation constant ($k_d$) of at least about $10^3$, about $10^4$, or about $10^5$ $m^{-1}$ $s^{-1}$; and (d) inhibits the binding of CTLA-4 to B7-1 (CD80) and B7-2 (CD86). Anti-CTLA-4 antibodies usable in the present invention include mAbs that bind specifically to human CTLA-4 and exhibit at least one, at least two or, in one embodiment, at least three of the preceding characteristics. An exemplary clinical anti-CTLA-4 antibody is the human mAb 10D1 (now known as ipilimumab and marketed as YERVOY®) as disclosed in U.S. Pat. No. 6,984,720. Ipilimumab is an anti-CTLA-4 antibody for use in the methods disclosed herein. Another anti-CTLA-4 antibody usable in the present methods is tremelimumab.

An exemplary clinical anti-CTLA-4 antibody useful for the combination is the human mAb 10D1 (now known as ipilimumab and marketed as YERVOY®) as disclosed in U.S. Pat. No. 6,984,720. Ipilimumab is an anti-CTLA-4 antibody for use in the methods disclosed herein. Ipilimumab is a fully human, IgG1 monoclonal antibody that blocks the binding of CTLA-4 to its B7 ligands, thereby stimulating T cell activation and improving overall survival (OS) in patients with advanced melanoma.

Another anti-CTLA-4 antibody useful for the present methods is tremelimumab (also known as CP-675,206). Tremelimumab is human IgG2 monoclonal anti-CTLA-4 antibody. Tremelimumab is described in WO/2012/122444, U.S. Publ. No. 2012/263677, or WO Publ. No. 2007/113648 A2.

Anti-CTLA-4 antibodies usable in the disclosed methods also include isolated antibodies that bind specifically to human CTLA-4 and cross-compete for binding to human CTLA-4 with ipilimumab or tremelimumab or bind to the same epitope region of human CTLA-4 as ipilimumab or tremelimumab. In certain embodiments, the antibodies that cross-compete for binding to human CTLA-4 with, or bind to the same epitope region of human CTLA-4 as does ipilimumab or tremelimumab, are antibodies comprising a heavy chain of the human IgG1 isotype. For administration to human subjects, these cross-competing antibodies are chimeric antibodies, or humanized or human antibodies. Usable anti-CTLA-4 antibodies also include antigen-binding portions of the above antibodies such as Fab, F(ab")$_2$, Fd or Fv fragments.

Ipilimumab (YERVOY®) is a fully human, IgG1 monoclonal antibody that blocks the binding of CTLA-4 to its B7 ligands, thereby stimulating T cell activation and improving overall survival (OS) in patients with advanced melanoma (Hodi et al. (2010) *N Engl J Med* 363:711-23). Concurrent therapy with nivolumab and ipilimumab in a Phase 1 clinical trial produced rapid and deep tumor regression in a substantial proportion of patients with advanced melanoma, and was significantly more effective than either antibody alone (Wolchok et al. (2013) *N Engl J Med* 369(2):122-33; WO 2013/173223). However, it was hitherto not known whether this combination of immunoregulatory antibodies would be similarly effective in other tumor types.

Anti-VEGF Antibody

In other embodiments, an anti-PD-1 antibody or anti-PD-L1 antibody is combined with an anti-VEGF antagonist, e.g., an anti-VEGF antibody. Vascular endothelial growth factor ("VEGF") is an endothelial cell-specific mitogen and an inducer of angiogenesis. VEGF has a prominent role in angiogenesis and tumor growth and development. In some embodiments of this invention, the anti-PD-1 antibody is administered in combination with an anti-VEGF antagonist. In certain embodiments, the anti-VEGF antagonist is an anti-VEGF antibody, antigen binding molecule or fragment thereof. In certain embodiments, the anti-VEGF antibody is bevacizumab (described in U.S. Pat. No. 7,169,901), or any other VEGF antibody known in the art including ranibizumab (U.S. Pat. No. 7,297,334), VGX-100 (U.S. Pat. No. 7,423,125), r84 (U.S. Pat. No. 8,034,905), aflibercept (U.S. Pat. No. 5,952,199), IMC-18F1 (U.S. Pat. No. 7,972,596), IMC-1C11 (PCT/US2000/02180), and ramucirumab (U.S. Pat. No. 7,498,414).

Chemotherapy and Platinum-Based Chemotherapy

In some embodiments, the anti-PD-1 antibody is administered in combination with any chemotherapy known in the art. In certain embodiments, the chemotherapy is a platinum based-chemotherapy. Platinum-based chemotherapies are coordination complexes of platinum. In some embodiments, the platinum-based chemotherapy is a platinum-doublet chemotherapy. In one embodiment, the chemotherapy is administered at the approved dose for the particular indication. In other embodiments, the chemotherapy is administered at any dose disclosed herein. In some embodiments, the platinum-based chemotherapy is cisplatin, carboplatin, oxaliplatin, satraplatin, picoplatin, Nedaplatin, Triplatin, Lipoplatin, or combinations thereof. In certain embodiments, the platinum-based chemotherapy is any other platinum-based chemotherapy known in the art. In some embodiments, the chemotherapy is the nucleotide analog gemcitabine. In an embodiment, the chemotherapy is a folate antimetabolite. In an embodiment, the folate antimetabolite is pemetrexed. In certain embodiments the chemotherapy is a taxane. In other embodiments, the taxane is paclitaxel. In other embodiments, the chemotherapy is a nucleoside analog. In one embodiment, the nucleoside analog is gemcitabine. In some embodiments, the chemotherapy is any other chemotherapy known in the art. In certain embodiments, at least one, at least two or more chemotherapeutic agents are administered in combination with the anti-PD-1 antibody, the anti-PD-L1 antibody or antigen-binding portion thereof. In an embodiment, an anti-CTLA-4 antibody is additionally administered.

Tyrosine Kinase Inhibitors

In certain embodiments, the anti-PD-1 antibody or an anti-PD-L1 antibody is administered in combination with a tyrosine kinase inhibitor. In certain embodiments, the tyrosine kinase inhibitor is gefitinib, erlotinib, combinations thereof or any other tyrosine kinase inhibitor known in the art. In some embodiments, the tyrosine kinase inhibitor act on the epidermal growth factor receptor (EGFR). In an embodiment, an anti-CTLA-4 antibody is additionally administered.

Pharmaceutical Compositions and Dosages

Therapeutic agents of the present invention can be constituted in a composition, e.g., a pharmaceutical composition containing an antibody and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. In one embodiment, the carrier for a composition containing an antibody is suitable for intravenous, intramuscular, subcutaneous, parenteral, spinal or epidermal administration (e.g., by injection or infusion), whereas the carrier for a composition containing a TKI is suitable for non-parenteral, e.g., oral, administration. A pharmaceutical composition of the invention can include one or more pharmaceutically acceptable salts, anti-oxidant, aqueous and non-aqueous carriers, and/or adjuvants such as preservatives, wetting agents, emulsifying agents and dispersing agents.

Dosage regimens are adjusted to provide the optimum desired response, e.g., a maximal therapeutic response and/or minimal adverse effects. In certain embodiments, the method of the present invention can be used with a flat dose or a weight-based dose. In further embodiments, the anti-PD-1 antibody, the anti-PD-L1 antibody, or antigen-binding portions thereof are administered as a flat dose. In further embodiments, the anti-PD-1 antibody, the anti-PD-L1 antibody, or antigen-binding portions thereof are administered as a weight-based dose. For administration of an anti-PD-1 antibody, as a monotherapy or in combination with another anti-cancer agent, the dosage can range from about 0.01 to about 20 mg/kg, about 0.1 to about 10 mg/kg, about 0.1 to about 5 mg/kg, about 1 to about 5 mg/kg, about 2 to about 5 mg/kg, about 7.5 to about 12.5 mg/kg, or about 0.1 to about 30 mg/kg of the subject's body weight or from about 80 mg to at least 800 mg, about 80 mg to at about 700 mg, about 80 mg to at about 600 mg, about 80 mg to at about 500 mg, about 80 mg to at about 400 mg, about 80 mg to at about 300 mg, about 100 mg to at about 300 mg, or about 200 mg to about 300 mg. For example, dosages can be about 0.1, about 0.3, about 1, about 2, about 3, about 5 or about 10 mg/kg body weight, or about 0.3, about 1, about 2, about 3, or about 5 mg/kg body weight; or about 80 mg, about 100 mg, about 160 mg, about 200 mg, about 240 mg, about 300 mg, about 320 mg, about 400 mg, about 500 mg, about 600 mg, about 700 mg, or about 800 mg. The dosing schedule is typically designed to achieve exposures that result in sustained receptor occupancy (RO) based on typical pharmacokinetic properties of an antibody. An exemplary treatment regime entails administration about once per week, once about every 2 weeks, once about every 3 weeks, once about every 4 weeks, once about a month, once about every 3-6 months or longer. In certain embodiments, an anti-PD-1 antibody such as nivolumab is administered to the subject once about every 2 weeks. In other embodiments, the antibody is administered once about every 3 weeks. The dosage and scheduling can change during a course of treatment. For example, a dosing schedule for anti-PD-1 monotherapy can comprise administering the Ab: (i) about every 2 weeks in about 6-week cycles; (ii) about every 4 weeks for about six dosages, then about every three months; (iii) about every 3 weeks; (iv) about 3-about 10 mg/kg once followed by about 1 mg/kg every about 2-3 weeks. Considering that an IgG4 antibody typically has a half-life of 2-3 weeks, a dosage regimen for an anti-PD-1 antibody of the invention comprises at least about 0.3 to at least about 10 mg/kg body weight, at least about 1 to at least about 5 mg/kg body weight, or at least about 1 to at least about 3 mg/kg body weight or at least about 80 to at least about 800 mg via intravenous administration, with the antibody being given every about 14-21 days in up to about 6-week or about 12-week cycles until complete response or confirmed progressive disease. In certain embodiments, an anti-PD-1 monotherapy is administered at 3 mg/kg every 2 weeks until progressive disease or unacceptable toxicity. In other embodiments, an anti-PD-1 monotherapy is administered at 240 mg every 2 weeks until progressive disease or unacceptable toxicity. In some embodiments, the antibody treatment, or any combination treatment disclosed herein, is continued for at least about 1 month, at least about 3 months, at least about 6 months, at least about 9 months, at least about 1 year, at least about 18 months, at least about 24 months, at least about 3 years, at least about 5 years, or at least about 10 years.

When used in combinations with other cancer agents, the dosage of an anti-PD-1 antibody can be lowered compared to the monotherapy dose. Dosages of nivolumab that are lower than the typical 3 mg/kg, but not less than 0.001 mg/kg, are subtherapeutic dosages. The subtherapeutic doses of an anti-PD-1 antibody used in the methods herein are higher than 0.001 mg/kg and lower than 3 mg/kg. In some embodiments, a subtherapeutic dose is about 0.001 mg/kg-about 1 mg/kg, about 0.01 mg/kg-about 1 mg/kg, about 0.1 mg/kg-about 1 mg/kg, or about 0.001 mg/kg-about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. In some embodiments, a subtherapeutic flat does is less than about 240 mg every 2 weeks, for instance about 160 mg or about 80 mg every two weeks. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%) (Brahmer et al. (2010) J Clin Oncol 28:3167-75). In some embodiments, 0.3 mg/kg dosing can allow for sufficient exposure to lead to maximal biologic activity.

In certain embodiments, the dose of an anti-PD-1 antibody (or an anti-PD-L1 antibody) is a fixed dose in a pharmaceutical composition. In other embodiments, the method of the present invention can be used with a flat dose (a dose given to a patient irrespective of the body weight of the patient). For example, a flat dose of a nivolumab can be about 240 mg. For example, a flat dose of pembrolizumab can be about 200 mg. In embodiments, the anti-PD-1 antibody or antigen-binding portion thereof is administered at a dose of about 240 mg. In embodiments, the anti-PD-1 antibody or antigen-binding portion thereof is administered at a dose of about 360 mg. In embodiments, the anti-PD-1 antibody or antigen-binding portion thereof is administered at a dose of about 480 mg. In one embodiment, 360 mg of the anti-PD-1 antibody or antigen binding fragment is administered once every 3 weeks. In another embodiment, 480 mg of the anti-PD-1 antibody or antigen binding fragment is administered once every 4 weeks.

For administration of an anti-PD-L1 antibody, as a monotherapy or in combination with another anti-cancer agent, the dosage can range from about 0.01 to about 20 mg/kg, about 0.1 to about 10 mg/kg, about 0.1 to about 5 mg/kg, about 1 to about 5 mg/kg, about 2 to about 5 mg/kg, about 7.5 to about 12.5 mg/kg, or about 0.1 to about 30 mg/kg of the subject's body weight or from about 80 mg to at least 800 mg, about 80 mg to at about 700 mg, about 80 mg to at about 600 mg, about 80 mg to at about 500 mg, about 80 mg to at about 400 mg, about 80 mg to at about 300 mg, about 100 mg to at about 300 mg, or about 200 mg to about 300 mg. For example, dosages can be about 0.1, about 0.3, about 1, about 2, about 3, about 5 or about 10 mg/kg body weight, or about 0.3, about 1, about 2, about 3, or about 5 mg/kg body weight; or about 80 mg, about 100 mg, about 160 mg, about 200 mg, about 240 mg, about 300 mg, about 320 mg, about 400 mg, about 500 mg, about 600 mg, about 700 mg, or about 800 mg. The dosing schedule is typically designed to achieve exposures that result in sustained receptor occupancy (RO) based on typical pharmacokinetic properties of an antibody. An exemplary treatment regime entails administration about once per week, about once every 2 weeks, about once every 3 weeks, about once every 4 weeks, about once a month, about once every 3-6 months or longer.

Although higher nivolumab monotherapy dosing up to about 10 mg/kg every two weeks has been achieved without reaching the maximum tolerated does (MTD), the significant toxicities reported in other trials of checkpoint inhibitors plus anti-angiogenic therapy (see, e.g., Johnson et al. (2013) *Cancer Immunol Res* 1:373-77; Rini et al. (2011) *Cancer* 117:758-67) support the selection of a nivolumab dose lower than 10 mg/kg.

In certain embodiments, the dose of an anti-PD-1 antibody (or an anti-PD-L1 antibody) is a fixed dose in a pharmaceutical composition.

Ipilimumab (YERVOY®) is approved for the treatment of melanoma at 3 mg/kg given intravenously once every 3 weeks for 4 doses. In certain embodiments, the dose of the anti-CTLA-4 antibody is a flat dose, which is given to a patient irrespective of the body weight. In a specific embodiment, the flat dose of the anti-CTLA-4 antibody is about 80 mg.

Thus, in some embodiments, about 3 mg/kg is the highest dosage of ipilimumab used in combination with the anti-PD-1 antibody though, in certain embodiments, an anti-CTLA-4 antibody such as ipilimumab can be dosed within the range of about 0.3 to about 10 mg/kg, about 0.5 to about 10 mg/kg, about 0.5 to about 5 mg/kg, or about 1 to about 5 mg/kg body weight about every two or three weeks when combined with nivolumab. In other embodiments, ipilimumab is administered on a different dosage schedule from nivolumab. In some embodiments, ipilimumab is administered about every week, about every two weeks, about every three weeks, about every four weeks, about every five weeks, about every six weeks, about every seven weeks, about every eight weeks, about every nine weeks, about every ten weeks, about every eleven weeks, about every twelve weeks or about every fifteen weeks.

Dosages of ipilimumab that are lower than the typical 3 mg/kg every 3 weeks, but not less than 0.001 mg/kg, are subtherapeutic dosages. The subtherapeutic doses of an anti-CTLA-4 antibody used in the methods herein are higher than 0.001 mg/kg and lower than 3 mg/kg. In some embodiments, a subtherapeutic dose is about 0.001 mg/kg-about 1 mg/kg, about 0.01 mg/kg-about 1 mg/kg, about 0.1 mg/kg-about 1 mg/kg, or about 0.001 mg/kg-about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. It has been shown that combination dosing of nivolumab at 3 mg/kg and ipilimumab at 3 mg/kg exceeded the MTD in a melanoma population, whereas a combination of nivolumab at 1 mg/kg plus ipilimumab at 3 mg/kg or nivolumab at 3 mg/kg plus ipilimumab at 1 mg/kg was found to be tolerable in melanoma patients (Wolchok et al. (2013) *N Engl J Med* 369(2):122-33). Accordingly, although nivolumab is tolerated up to 10 mg/kg given intravenously every 2 weeks, in certain embodiments doses of the anti-PD-1 antibody do not exceed about 3 mg/kg when combined with ipilimumab. In certain embodiments, based on risk-benefit and PK-PD assessments, the dosage used comprises a combination of nivolumab at about 1 mg/kg plus ipilimumab at about 3 mg/kg, nivolumab at about 3 mg/kg plus ipilimumab at about 1 mg/kg, or nivolumab at about 3 mg/kg plus ipilimumab at about 3 mg/kg is used, each administered at a dosing frequency of once about every 2-4 weeks, in certain embodiments, once about every 2 weeks or once about every 3 weeks. In certain other embodiments, nivolumab is administered at a dosage of about 0.1, about 0.3, about 1, about 2, about 3 or about 5 mg/kg in combination with ipilimumab administered at a dosage of about 0.1, about 0.3, about 1, about 2, about 3 or about 5 mg/kg, once about every 2 weeks, once about every 3 weeks, or once about every 4 weeks. In further embodiments the dosage used comprises a combination of nivolumab at about 240 mg plus ipilimumab at about 80 mg, nivolumab at about 240 mg plus ipilimumab at about 240 mg, or nivolumab at about 80 mg plus ipilimumab at about 240 is used, each administered at a dosing frequency of once about every 2-4 weeks, in certain embodiments, once about every 2 weeks or once about every 3 weeks. In certain other embodiments, nivolumab is administered at a dosage of about 40 mg, about 80 mg, about 100 mg, about 160 mg, about 200 mg, about 240 mg, about 320 mg or about 400 mg in combination with ipilimumab administered at a dosage of about 40 mg, about 80 mg, about 160 mg, about 240 mg, about 320 mg or about 400 mg, once about every 2 weeks, once about every 3 weeks, or once about every 4 weeks.

In certain embodiments, the combination of an anti-PD-1 antibody or anti-PD-L1 antibody and an anti-CTLA-4 antibody is administered intravenously to the subject in an induction phase about every 2 or 3 weeks for 1, 2, 3 or 4 administrations. In certain embodiments, the combination of an anti-PD-1 antibody and an anti-PD-L1 antibody is administered intravenously in the induction phase about every 2 weeks or about every 3 weeks for about 4 administrations. The induction phase is followed by a maintenance phase during which only the anti-PD-1 antibody or anti-PD-L1 antibody is administered to the subject at a dosage of about 0.1, about 0.3, about 1, about 2, about 3, about 5 or about 10 mg/kg or about 40 mg, about 80 mg, about 100 mg, about 160 mg, about 200 mg, about 240 mg, about 320 mg or about 400 mg about every two or three weeks for as long as the treatment proves efficacious or until unmanageable toxicity or disease progression occurs. In certain embodiments, nivolumab is administered during the maintenance phase at a dose of about 3 mg/kg body weight or about 240 mg about every 2 weeks.

In certain embodiments, the dose of an anti-PD-1 antibody or an anti-PD-L1 antibody is a fixed dose in a pharmaceutical composition with a second anti-cancer agent. In certain embodiments, the anti-PD-1 antibody or the anti-PD-L1 antibody and the anti-CTLA-4 antibody is formulated as a single composition, wherein the dose of the anti-PD-1 antibody or the anti-PD-L1 antibody and the dose of the anti-CTLA-4 antibody are combined at a ratio of 1:50, 1:40, 1:30, 1:20, 1:10. 1:5, 1:3, 1:1, 3:1, 5:1, 10:1, 20:1, 30:1, 40:1, or 50:1.

For combination of nivolumab with other anti-cancer agents, these agents are administered at their approved dosages. Treatment is continued as long as clinical benefit is observed or until unacceptable toxicity or disease progression occurs. Nevertheless, in certain embodiments, the dosages of these anti-cancer agents administered are significantly lower than the approved dosage, i.e., a subtherapeutic dosage, of the agent is administered in combination with the anti-PD-1 antibody or anti-PD-L1 antibody. The anti-PD-1 antibody or anti-PD-L1 antibody can be administered at the dosage that has been shown to produce the highest efficacy as monotherapy in clinical trials, e.g., about 3 mg/kg of nivolumab administered once about every three weeks (Topalian et al. (2012a) *N Engl J Med* 366:2443-54; Topalian et al. (2012b) *Curr Opin Immunol* 24:207-12), at a significantly lower dose, i.e., at a subtherapeutic dose, or at a flat dose, i.e., 240 mg. In certain embodiments, the anti-PD-1 antibody is administered at about 3 mg/kg or 240 mg once about every two weeks.

In certain embodiments, the anti-PD-1 antibody or anti-PD-L1 antibody is administered in combination with the standard of care for the particular type of cancer. In further embodiments, the anti-PD-1 antibody or anti-PD-L1 antibody is administered in combination with chemotherapy, including 5-FU, etoposide and platinum-based drugs, for example carboplatin or cisplatin. In some embodiments, the anti-PD-1 antibody or anti-PD-L1 antibody is administered before, concurrently or after radiation therapy. In some embodiments, the anti-PD-1 antibody or anti-PD-L1 antibody is administered before, concurrently or after surgical resection.

Dosage and frequency vary depending on the half-life of the antibody in the subject. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is typically administered at relatively infrequent intervals over a long period of time. Some patients continue to receive treatment for the rest of their lives. In therapeutic applications, a relatively high dosage at relatively short intervals is sometimes required until progression of the disease is reduced or terminated, or until the patient shows partial or complete amelioration of symptoms of disease. Thereafter, the patient can be administered a prophylactic regime.

Actual dosage levels of the active ingredient or ingredients in the pharmaceutical compositions of the present invention can be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present invention can be administered via one or more routes of administration using one or more of a variety of methods well known in the art. As will be appreciated by the skilled artisan, the route and/or mode of administration will vary depending upon the desired results.

Kits

Also within the scope of the present invention are kits comprising an immune checkpoint inhibitor (e.g., an anti-PD-1 antibody or and anti-PD-L1 antibody) and, optionally, another anti-cancer agent for therapeutic uses. Kits typically include a label indicating the intended use of the contents of the kit and instructions for use. The term label includes any writing, or recorded material supplied on or with the kit, or which otherwise accompanies the kit. In some embodiments, the invention is directed to a kit for treating a subject afflicted with a tumor derived from an HPV positive SCCHN, the kit comprising: (a) an immune checkpoint inhibitor (e.g., an anti-PD-1 antibody or antigen-binding portion thereof or an anti-PD-L1 antibody or antigen-binding portion thereof); (b) instructions for determining the HPV positivity of the tumor and, if the tumor is positive for HPV, administering the immune checkpoint inhibitor (e.g., the anti-PD-1 antibody or antigen-binding portion thereof or the anti-PD-L1 antibody or antigen-binding portion thereof) to the subject in the methods disclosed herein. In some embodiment, the kit further comprises an agent to determine the HPV positivity of the tumor. In certain embodiments, the HPV positivity is measured by an expression of HPV p16. In certain embodiments, the invention is directed to a kit for treating a subject afflicted with a tumor derived from an HPV negative SCCHN, the kit comprising: (a) an immune checkpoint inhibitor (e.g., an anti-PD-1 antibody or antigen-binding portion thereof or an anti-PD-L1 antibody or antigen-binding portion thereof); (b) instructions for determining the HPV negativity of the tumor and, if the tumor is negative for HPV, administering the immune checkpoint inhibitor (e.g., the anti-PD-1 antibody or antigen-binding portion thereof or the anti-PD-L1 antibody or antigen-binding portion thereof) to the subject in the methods disclosed herein. In some embodiment, the kit further comprises an agent to determine the HPV negativity of the tumor. In certain embodiments, the HPV negativity is measured by an expression of HPV p16. In further embodiments, the kit comprises one or more additional anti-cancer agents, for example an anti-CTLA-4 antibody and/or a TKI. In certain embodiments, the anti-PD-1 antibody, the anti-PD-L1 antibody, the anti-CTLA-4 antibody and/or the TKI can be co-packaged in unit dosage form. In certain embodiments for treating human patients, the kit comprises an anti-human PD-1 antibody or anti-human PD-L1 antibody disclosed herein, e.g., nivolumab or pembrolizumab. In other embodiments, the kit comprises an anti-human CTLA-4 antibody disclosed herein, e.g., ipilimumab or tremelimumab.

The present invention is further illustrated by the following example, which should not be construed as further limiting. The contents of all references cited throughout this application are expressly incorporated herein by reference.

Example 1

A non-comparative, two-cohort, single-arm, open-label, phase 1/2 study of nivolumab will be performed in subjects with virus-positive and virus-negative solid tumors to evaluate the safety, tolerability, and efficacy of nivolumab in subjects with select virus-positive and virus-negative tumors. Subjects will receive a flat dose of 240 mg nivolumab administered by IV over 30 minutes every two weeks until progression or unacceptable toxicity. Efficacy will measured by objective response rate and duration of response.

The study will include two cohorts: a neoadjuvant cohort and a metastatic/recurrent cohort. The primary objective of the neoadjuvant cohort will be to investigate the safety and tolerability of neoadjuvant nivolumab administration in the following tumor types: HPV-positive squamous cell cancer of the head and neck (SCCHN); HPV-negative SCCHN; Merkel cell carcinoma (MCC); and cervical, vaginal, or vulvar cancers (GYN). The primary objective of the metastatic/recurrent cohort will be to evaluate the investigator-assessed objective response rate (ORR) of nivolumab monotherapy (240 mg flat dose by IV every two weeks) in subjects with the following diseases: metastatic or recurrent nasopharyngeal carcinoma (NPC); metastatic or recurrent EBV related gastric; metastatic or recurrent Merkel cell carcinoma; metastatic or recurrent cervical, vaginal, or vulvar cancers; and metastatic or recurrent HPV-positive SCCHN.

The secondary objective of the neoadjuvant cohort will be to determine the percent change from baseline of immune cells and the percent change from baseline of selected immune activation/inhibitory molecules of viral specific T cells in tumor specific subsets of nivolumab-treated subjects. The secondary objective of the metastatic/recurrent cohort will be to evaluate the progression-free survival and overall survival in subjects with nivolumab monotherapy.

Patients in the neoadjuvant cohort will be evaluated for progression-free survival up to 1 year after neoadjuvant administration of nivolumab. Patients will further be monitored to determine the percent change from baseline in tumor volume after two flat doses of 240 mg neoadjuvant nivolumab. Pathologic complete response of tumors will also be determined in subjects who receive surgical resection after two doses of neoadjuvant nivolumab in SCCHN, resectable Merkel cell Carcinoma, and cervical, vaginal, or vulvar cancer.

In the metastatic/recurrent cohort, the safety and tolerability, defined as toxicity rates (worst CTC grade per subject) of adverse events and specific laboratory tests, of nivolumab monotherapy in subjects with metastatic or recurrent viral-mediated tumors will also be monitored.

In both cohorts, changes in anti-viral and anti-tumor immune responses at the tumor site will be evaluated using proliferative and/or functional assays. Study administrators will also investigate the potential association between selected biomarker measures in peripheral blood and tumor tissue, including PD-L1, with safety and clinical efficacy measures and the pharmacodynamic activity of nivolumab in the peripheral blood and tumor tissue as measured by gene expression, flow cytometry, immunohistochemistry and soluble factor assays. Subjects will further be observed to study the effect of nivolumab on the viral antigen specific T cell responsiveness in the peripheral blood and the potential association between the number of tumor mutations and neoantigens with clinical efficacy measures and whether tumor antigen-specific T cells are present in the periphery. Further, the pre- and post-treatment Epstein-Barr virus (EBV) DNA levels in subjects with EBV-positive gastric cancer and nasopharyngeal carcinoma will be evaluated in these patients.

In addition, all subjects will be evaluated as to overall health status as assessed by the EQ-5D and cancer specific health related quality of life as assessed by EORTC QLQ-C30. In all cases, the immunogenicity and pharmacokinetics of nivolumab monotherapy will be characterized, and the exposure-response relationships will be explored, when possible.

Subjects

All eligible patients will have histopathologic confirmed Merkel cell carcinoma; EBV-positive gastric or gastro-esophageal junction carcinoma (including adenocarcinoma arising from the lower esophagus); nasopharyngeal carcinoma; squamous cell carcinoma of the cervix, vagina, or vulva; or SCCHN. For subjects with Merkel cell carcinoma, Merkel cell polyomavirus (MCPyV) status will be determined after enrollment. For subjects in the metastatic cohort with gastric tumor types, EBV positivity is defined by EBV-encoded RNA (EBER) in situ hybridization. For subjects in the metastatic cohort with nasopharyngeal carcinoma tumor types, EBV positivity is as defined by EBER in situ hybridization, and virus testing will be performed retrospectively only if results from prior testing are not available. For subjects in the metastatic cohort with gynecological tumors, HPV positivity is defined by in situ hybridization, real-time PCR, or immunohistochemistry (IHC). High-risk HPV positivity includes the following subtypes: 16, 18, 31, 33, 35, 39, 45, 51, 52, 56, 58, 59, 66, 68. Virus testing will be performed retrospectively only if results from prior testing are not available. For subjects in the virus-positive neoadjuvant and metastatic cohorts with squamous cell carcinoma of the head and neck, HPV positivity is defined by HPV p16 in situ hybridization, IHC, or tumor sequencing, and HPV p16 IHC should be interpreted as positive if >70% strong and diffuse nuclear and cytoplasmic staining is specific to tumor cells. HPV positive status can be obtained from either the primary tumor or metastatic lymph node. For subjects in the virus negative neoadjuvant cohort HPV negativity should be documented by HPV p16 in situ hybridization, IHC, or tumor sequencing.

Subjects in the neoadjuvant cohort can include those with SCCHN for whom surgical resection is planned. These subjects must have newly diagnosed, histologically or cytologically confirmed squamous cell carcinoma or undifferentiated carcinoma of the oropharynx, and subjects must have been determined to have resectable disease. The biopsy can have been obtained from the primary tumor or metastatic lymph node. In addition, these subjects must have T2 or greater primary lesions, N2 or greater nodal disease, and greater than 10 pack/year smoking history.

Squamous cell cervical, vulvar, or vaginal cancer subjects of the neoadjuvant cohort will include those with stage II to IVA cervical cancer who have planned surgical staging or chemotherapy/radiation treatment or those with stage II to IVA vulvar or vaginal cancer who have planned curative intent surgery or chemotherapy/radiation treatment.

Subjects with Merkel cell carcinoma in the neoadjuvant cohort must have a tumor amenable to pre-treatment biopsy (core needle); post treatment biopsy will consist of the operative specimen. In addition, subjects will have resectable disease tumors characterized as stage IIA-IIIB disease with a primary tumor≥2 cm or of any size with palpable regional lymph node metastases or resectable in-transit metastases, stage IV disease with resectable limited metastasis, or local/regional recurrent disease as defined as total burden≥1 cm diameter with resectable disease defined by local or institutional surgical practices.

Subjects in the metastatic/recurrent cohort will include subjects with progressive metastatic or recurrent disease treated with no more than two prior systemic therapies. These subjects will have a measurable disease by CT or MRI per RECIST 1.1 criteria (radiographic tumor assessment must be performed within 35 days prior to first dose). Subjects who actively refuse chemotherapy or other standard therapies for the treatment of unresectable or metastatic disease (advanced Stage III or Stage IV) can also be included in this cohort. Subjects in the metastatic/recurrent cohort will be selected from those having histologically confirmed gastric or gastro-esophageal junction carcinoma (including adenocarcinoma arising from the lower esophagus) who are EBV positive; histologically confirmed HPV-positive SCCHN (oral cavity, pharynx, larynx) not amenable to local therapy with curative intent (surgery or radiation therapy with or without chemotherapy); histologically confirmed HPV-positive cervical, vulvar, or vaginal cancer; histologically confirmed Merkel cell carcinoma, including those with no prior systemic treatment; and histologically confirmed EBV-positive nasopharyngeal carcinoma, excluding HPV associated nasopharyngeal carcinoma and keratinizing squamous cell carcinoma (WHO Type I).

Subjects in both cohorts will be required to be 18 years or older and to have an Eastern Cooperative Oncology Group (ECOG) performance status of 0 or 1. Subjects must be willing to provide tumor tissue (archival or fresh biopsy specimen) for PD-L1 expression analysis and other biomarker correlative studies. The biopsy should be excisional, incisional, or core needle. Fine needle aspirates are insufficient.

Subjects with active brain metastases or leptomeningeal metastases will be excluded from the study, unless the brain metastases have been treated and there has been no MRI evidence of progression for at least 4 weeks after treatment is complete and within 28 days prior to first dose of study drug administration. There must also be no requirement for immunosuppressive doses of systemic corticosteroids (>10 mg/day prednisone equivalents) for at least 2 weeks prior to study drug administration.

Subjects will further be excluded if any of the following applies: any serious or uncontrolled medical disorder that, in the opinion of the investigator, can increase the risk associated with study participation or study drug administration, impair the ability of the subject to receive protocol therapy, or interfere with the interpretation of study results; active, known, or suspected autoimmune disease (excluding vitiligo, type I diabetes mellitus, residual hypothyroidism due to autoimmune condition only requiring hormone replacement, or conditions not expected to recur in the absence of an external trigger); a condition requiring systemic treatment with either corticosteroids (>10 mg daily prednisone equivalents) or other immunosuppressive medications within 14 days of study drug administration (inhaled or topical steroids, and adrenal replacement doses are permitted in the absence of active autoimmune disease); primary tumor or nodal metastasis fixed to the carotid artery, skull base or cervical spine; prior therapy with experimental anti-tumor vaccines, any T cell co-stimulation or checkpoint pathways, such as anti-PD-1, anti-PD-L1, anti-PD-L2, anti-CD137, or anti-CTLA-4 antibody, including ipilimumab, or other medicines specifically targeting T cells; toxicities attributed to prior anti-cancer therapy other than alopecia and fatigue must have resolved to Grade 1 (NCI CTCAE version 4) or baseline before administration of study drug (subjects with toxicities attributed to prior anti-cancer therapy which are not expected to resolve and result in long lasting sequelae, such as neuropathy after platinum based therapy, are permitted to enroll); prior treatment with any chemotherapy, radiation therapy, biologics for cancer, or investigational therapy within 28 days of first administration of study treatment (subjects with prior cytotoxic or investigational products<4 weeks prior to treatment might be eligible after discussion between investigator and sponsor, if toxicities from the prior treatment have been resolved to Grade 1 (NCI CTCAE version 4); and a positive test for hepatitis B virus surface antigen (HBV sAg) or hepatitis C virus (ribonucleic acid or HCV antibody) indicating acute or chronic infection; known history of testing positive for human immunodeficiency virus (HIV) or known acquired immunodeficiency syndrome (AIDS); history of allergy to study drug components, history of severe hypersensitivity reaction to any monoclonal antibody; women of childbearing potential who are pregnant or breastfeeding or women with a positive pregnancy test at enrollment prior to administration of study medication.

Study Design and Treatment

This study will be an open-label, multi-center, phase 1/2 trial to investigate the safety and efficacy of nivolumab as a single agent in selected virus-positive and virus-negative solid tumors. The neoadjuvant cohort will comprise 84 subjects in 3 tumor types (FIG. 1). This cohort will serve to investigate the safety and tolerability of neoadjuvant nivolumab administration.

Enrollment for each tumor type in the neoadjuvant cohort will pause after the first 10 subjects are enrolled to assess safety and determine the number of subjects with chemotherapy/radiation (GYN patients where appropriate) or surgical (SCCHN, MCC, and GYN patients) delays beyond 4 weeks from the planned date (FIG. 1). If ≥3 of the first 10 subjects for a single tumor type have delays beyond 4 weeks from the planned surgery date or planned start date for chemoradiation due to a nivolumab immune-related adverse event(s) specified in the label, that specific tumor cohort will close. The remaining tumor types in the neoadjuvant cohort will not close enrollment should tumor type(s) close due to a delay in surgery due to nivolumab. If the first 8 patients for a single tumor type experience no delay, a pause in enrollment will not be required.

The neoadjuvant cohort will enroll 3 tumor types: HPV-positive and HPV-negative SCCHN, HPV-positive cervical/vaginal/vulvar cancers, and polyomavirus-associated Merkel cell carcinoma. The SCCHN tumor types will require prospective (prior to study drug assignment) testing of virus positivity. Twenty-one virus-positive and 21 virus-negative SCCHN subjects will be enrolled. The other tumor types will not require prospective virus testing for entry, given the high (>85% positivity) infectivity. The virus-negative group will serve as a control group for the biological analysis. Subjects will have an initial biopsy, receive 2 flat doses of 240 mg nivolumab by intravenous (IV) infusion over 30 minutes on day 1 and day 15, followed by a surgical resection or chemotherapy/radiation (FIG. 1; Table 1). No other pre-surgical therapy is allowed.

TABLE 1

Nivolumab Dosing Summary
Nivolumab Dosing

| Cohort | Drug | Dose | Frequency of administration | Route of administration | Duration |
|---|---|---|---|---|---|
| Neoadjuvant | Nivolumab | 240 mg flat dose | Day 1, Day 15 | 30 minute Intravenous (IV) infusion | Two doses |
| Metastatic | Nivolumab | 240 mg flat dose | every 2 weeks | 30 minute Intravenous (IV) infusion | Until progression, toxicity, or discontinuation from study |
| Subjects Treated with Nivolumab Post-Standard of Care | Nivolumab | 240 mg flat dose | every 2 weeks | 30 minute Intravenous (IV) infusion | Until progression, toxicity, or discontinuation from study |

Select subjects initially treated with nivolumab will receive subsequent standard of care treatment. Following the standard of care treatment, subjects can receive recurrent treatment of a flat dose of 240 mg nivolumab by IV every two weeks until disease progression, toxicity, or discontinuation from the study (Table 1).

The recurrent/metastatic cohort, will comprise 115 subjects in 5 tumor types (FIG. 1). This cohort will server to evaluate the investigator-assessed ORR of nivolumab monotherapy.

The Metastatic Cohort will enroll subjects in the metastatic or recurrent setting with their disease. This cohort will be comprised of the 5 following tumor types: EBV-related gastric, EBV-related nasopharyngeal, HPV-positive SCCHN, HPV-positive cervical/vulvar/vaginal, and polyomavirus-associated Merkel cell carcinoma. The SCCHN and gastric tumor types will require prospective testing of virus positivity. A flat dose of 240 mg nivolumab will be administered by IV over 30 minutes every two weeks until unacceptable toxicity or disease progression as defined by RECIST 1.1 (Table 1).

Assessments

Safety assessments at baseline will include a medical history to be obtained to capture relevant underlying conditions. Baseline examinations should include signs and symptoms, weight, height, ECOG Performance Status, blood pressure (BP), heart rate (HR), temperature, respiratory rate, and oxygen saturation by pulse oximetry at rest and after exertion should be performed within 14 days prior to first dose. Concomitant medications will also be collected from within 14 days prior to first dose and through the study treatment. Baseline safety laboratory assessments should be done within 14 days prior to the first dose.

Subjects will be evaluated for safety if they have received any study drug. Toxicity assessments will be performed continuously during the treatment phase. On-study assessments including weight, height, ECOG Performance Status, BP, HR, temperature, respiratory rate, and oxygen saturation by pulse oximetry at rest and after exertion will be performed. On-study safety laboratory assessments will also be performed.

Efficacy will be assessed by tumor imaging for ongoing study treatment decisions by the investigator using RECIST (Response Evaluation Criteria in Solid Tumors) 1.1 criteria.

Statistical Analysis

Sample size determination will not be based on statistical power calculation. For the neoadjuvant cohort, the SCCHN tumor types will contain 21 HPV-positive and 21 HPV-negative subjects. MCC and HPV-positive cervical, vaginal, or vulvar cancers tumor types will contain 21 subjects each. A sample size of 21 can detect, with more than 66% and 89% probability, a safety event that occurs at an incident rate of 5% and 10%, respectively. Assuming 10%, 15%, and 20% for pathologic complete response rate, a sample size of 21 can detect, more than 89%, 97% and 99% probability, at least one pathologic complete response respectively.

For the recurrent/metastatic cohort, each specific disease or tumor type in the recurrent/metastatic cohort will contain 23 subjects. Table 2 shows the probabilities of observing 0, 1, or 2 responders and ≥3 responders assuming 5%, 20%, and 30% true response rate of ORR. Table 3 shows two-sided 95% exact CI using Clopper-Pearson methods based on observed 3, 4, and 5 responders out of 23 subjects.

TABLE 2

Probability of observing responses given true ORR

| True response rate of ORR | Probability of observing 0, 1 or 2 responses | Probability of observing ≥3 responses |
|---|---|---|
| 5% | 89.5% | 10.5% |
| 20% | 13.3% | 86.7% |
| 30% | 1.6% | 98.4% |

TABLE 3

Two-sided 95% exact CI using Clopper-Pearson method based on number of observed responses out of 23 subjects

| | The number of observed responses | | |
|---|---|---|---|
| | 3 | 4 | 5 |
| Observed Response Rate | 3/23 (13.0%) | 4/23 (17.4%) | 5/23 (21.7%) |
| 95% exact CI | (2.8%, 33.6%) | (5.0%, 38.8%) | (7.5%, 43.7%) |

Endpoints and Analyses

The primary objective of neoadjuvant cohort is the safety assessment. All recorded adverse events will be listed and tabulated by system organ class, preferred term, and cohort/arm and coded according to the most current version of MedDRA. The incidence of adverse events will be reviewed for potential significance and clinical importance. Vital signs and clinical laboratory test results will be listed and summarized by cohort/arm. Any significant physical examination findings and results of clinical laboratory tests will be listed. The incidence of infusion reactions will be reviewed to assess the safety and tolerability of reduced infusion times for nivolumab. The proportion of subjects in the biopsy/neoadjuvant cohort with surgery delayed>4 weeks due to a drug-related AE will be reported for each tumor type.

The primary objective of the metastatic/recurrent cohort is determination of the investigator-assessed ORR, defined as the number of subjects with a best overall response (BOR) of confirmed complete response (CR) or partial response (PR) divided by the number of treated subjects. BOR is defined as the best response designation recorded between the date of first dose and the date of the initial objectively documented tumor progression per investigator assessment using RECIST 1.1 criteria or the date of the last tumor assessment date prior to subsequent therapy.

The investigator assessed ORR in the metastatic cohort will be summarized by binomial response rates and their corresponding two-sided 95% exact CIs using Clopper-Pearson method. The DOR will be summarized subjects who achieve confirmed PR or CR DOR is defined as the time from first confirmed response (CR or PR) to the date of the initial objectively documented tumor progression as determined per investigator assessment using RECIST 1.1 criteria or death due to any cause, whichever occurs first. For subjects who neither progress nor die, the DOR will be censored on the date of their last evaluable tumor assessment. DOR will only be evaluated in subjects with objective response of CR or PR.

Time to event distribution will be estimated using Kaplan Meier techniques. This will be done for PFS (based on investigator assessments) and OS. Median PFS or OS along with 95% CI will be constructed based on a log-log transformed CI for the survivor function. Rates at some fixed timepoints will be derived from the Kaplan Meier estimate and corresponding confidence interval will be derived based on Greenwood formula for variance derivation and on log-log transformation applied on the survivor function.

The pharmacodynamic effects of nivolumab on selected biomarkers will be assessed by summary statistics and corresponding changes (or percent changes) from baseline tabulated by time and cohort. In addition, the time course of biomarker outcomes will be investigated graphically, by summary plots or individual subject plots. If there is an indication of a meaningful pharmacodynamic trend, methods such as linear mixed models can be used to characterize the pattern of change over time. The potential association between PD-L1 expression level (IHC) and clinical efficacy measures will be assessed using Fisher's exact test or other methodology as appropriate.

Potential associations of various biomarker measures with pharmacokinetic exposure, safety and clinical efficacy measures will be investigated based on data availability. Methods such as, but not limited to, logistic regression and graphical summaries can be used to assess these associations.

What is claimed is:

1. A method for treating a human subject afflicted with a tumor derived from a human papilloma virus (HPV)-positive squamous cell carcinoma head and neck cancer (SCCHN) comprising administering to the subject a flat dose of 480 mg of nivolumab once every four weeks without regard for the weight of the subject.

2. A method of treating a human subject afflicted with a tumor derived from an HPV-positive SCCHN comprising:
   (i) measuring a level of HPV in a sample of the subject, wherein the subject is positive for HPV; and
   (ii) administering to the subject a flat dose of 480 mg of nivolumab once every four weeks without regard for the weight of the subject.

3. The method of claim 1, wherein the HPV-positive SCCHN comprises a tumor expressing one or more proteins derived from an HPV or comprising a nucleotide sequence encoding the one or more proteins.

4. The method of claim 3, wherein the one or more proteins derived from an HPV comprise p16, Ki-67, Cyclin D1, p53, ProEx C, E6, E7, or any combination thereof.

5. The method of claim 1, wherein the HPV comprises HPV subtype 16, 18, 31, 33, 35, 39, 45, 51, 52, 56, 58, 59, 66, 68, or any combination thereof.

6. The method of claim 1, wherein more than about 70% of tumor cells in the tumor show strong and diffuse nuclear and cytoplasmic staining by an immunohistochemistry against p16.

7. The method of claim 1, wherein the tumor further expresses PD-L1.

8. The method of claim 1, wherein the subject exhibits an overall survival of at least about 10 months after the administration.

9. The method of claim 1, which further comprises administering one or more additional anti-cancer agents.

10. The method of claim 9, wherein at least one of the anti-cancer agents is selected from the group consisting of (i) an antibody or antigen-binding portion thereof that binds specifically to a CTLA-4 and inhibits CTLA-4 activity, (ii) a chemotherapy, (iii) a platinum-based doublet chemotherapy, (iv) a tyrosine kinase inhibitor, (v) an anti-VEGF inhibitor, and (vi) any combination thereof.

11. The method of claim 1, wherein the subject received one or more anti-cancer agents prior to the administration of the nivolumab.

12. The method of claim 11, wherein the one or more anti-cancer agents were not effective in treating the tumor.

13. The method of claim 12, wherein the one or more anti-cancer agents comprise a platinum-based therapy.

14. The method of claim 2, wherein the subject exhibits an overall survival of at least about 10 months after the administration.

15. The method of claim 2, wherein the HPV-positive SCCHN comprises a tumor expressing one or more proteins derived from an HPV or comprising a nucleotide sequence encoding the one or more proteins.

16. The method of claim 15, wherein the one or more proteins derived from an HPV comprise p16, Ki-67, Cyclin D1, p53, ProEx C, E6, E7, or any combination thereof.

17. The method of claim 2, wherein the HPV comprises HPV subtype 16, 18, 31, 33, 35, 39, 45, 51, 52, 56, 58, 59, 66, 68, or any combination thereof.

18. The method of claim 2, wherein more than about 70% of tumor cells in the tumor show strong and diffuse nuclear and cytoplasmic staining by an immunohistochemistry against p16.

19. The method of claim 2, wherein the tumor further expresses PD-L1.

* * * * *